United States Patent
Resconi et al.

(10) Patent No.: US 6,369,254 B1
(45) Date of Patent: Apr. 9, 2002

(54) BRIDGED METALLOCENE COMPOUNDS, PROCESSES FOR THE PREPARATION THEREOF AND USE THEREOF IN CATALYSTS FOR THE POLYMERIZATION OF OLEFINS

(75) Inventors: Luigi Resconi, Ferrara (IT); Ilya E. Nifant'ev, Moscow (RU); Yuri A. Dubitsky, Santa Maria Maddalena; Elisabetta Barbassa, Sesto Calende, both of (IT); Colin J. Schaverien, Amsterdam; Ren' Ernst, Hoorn, both of (NL)

(73) Assignee: Basell Technology Company BV, Hoofddorp (NL)

( * ) Notice: Subject to any disclaimer, the term of this patent is extended or adjusted under 35 U.S.C. 154(b) by 151 days.

(21) Appl. No.: 08/655,729

(22) Filed: May 30, 1996

(30) Foreign Application Priority Data

May 30, 1995 (IT) .......................... MI95A1118

(51) Int. Cl.[7] .............................. C08F 4/64; C08F 4/642; C08F 4/68; C08F 4/69
(52) U.S. Cl. .............................. 556/11; 556/13; 556/43; 556/53; 556/58; 502/117; 502/152; 526/127; 526/160; 526/943
(58) Field of Search ................................ 556/9, 11, 12, 556/13, 42, 43, 51, 52, 53, 57, 58; 502/155; 526/127, 160, 943

(56) References Cited

U.S. PATENT DOCUMENTS 5,594,081 A * 1/1997 Uchino et al. .............. 526/127

FOREIGN PATENT DOCUMENTS

| EP | A 327 414 | 12/1989 |
| EP | A 485 823 | 11/1991 |
| EP | A 524 624 | 7/1992 |
| EP | A 604 908 | 12/1993 |
| EP | 0 693 502 A1 | 1/1996 |
| EP | 0 704 461 A2 | 4/1996 |
| WO | WO 94/11406 | 5/1994 |
| WO | WO 96/04317 | 2/1996 |

* cited by examiner

*Primary Examiner*—David W. Wu
*Assistant Examiner*—R. Rabago
(74) *Attorney, Agent, or Firm*—Bryan Cave LLP

(57) ABSTRACT

Metallocene compounds with two indenyl-type ligands linked in the 4 position by means of a divalent bridging group can be suitably used as components of catalysts for the polymerization of olefins. In particular, it is possible to prepare saturated or unsaturated elastomeric copolymers of ethylene characterized by valuable properties, such as low ash content and uniform distribution of the comonomers in the polymer chain. Metallocenes of the following generic structure are disclosed:

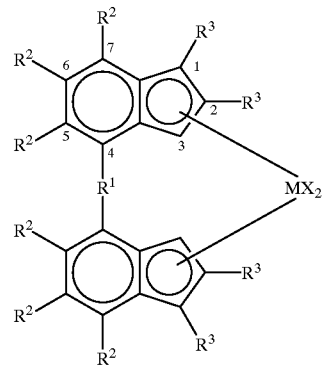

6 Claims, No Drawings

BRIDGED METALLOCENE COMPOUNDS, PROCESSES FOR THE PREPARATION THEREOF AND USE THEREOF IN CATALYSTS FOR THE POLYMERIZATION OF OLEFINS

BACKGROUND OF THE INVENTION

1. Field of the Invention

The present invention relates to bridged metallocene compounds, to the corresponding ligands, to processes for preparing them and to the use of said metallocenes as components of catalysts for the polymerization of olefins.

2. Description of Related Art

Stereorigid chiral metallocene compounds possessing two bridged indenyl groups are known. They are used as components of catalysts for the polymerization of olefins, in particular for the preparation of stereo-regular polyolefins.

The numbering of the substituents on the indenyl group, to which reference is made in the present application, is as follows:

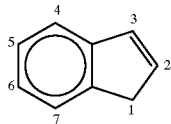

In metallocene compounds of the type indicated above, the indenyl groups are linked together by divalent radicals that have two or more carbon atoms, such as $(CH_2)_2$ groups, or with atoms other than carbon, such as dimethylsilanediyl groups, which are generally joined to the indenyl rings in the 1 position. See, for example, European Patent Application EP-A-485 823.

European Patent Application EP-A-372 414 indicates two specific bis-indenyl metallocene compounds in which the divalent group linking the two indenyl ligands is joined in the 1 position to one indenyl ring and in the 2 position to the other indenyl ring (page 5, formulae II-1 and II-2).

International Patent Application WO 94/11406 describes a class of metallocene compounds comprising indenyl groups substituted in the 2 position. In particular, bis-indenyl compounds bridged in the 2 position on the indenyl rings are described.

SUMMARY OF THE INVENTION

New metallocene compounds have now been found which have two indenyl-type ligands linked together by a divalent group in the 4 position, and which can advantageously be used as catalyst components for the polymerization of olefins.

Therefore, in accordance with an aspect of the present invention, there are provided metallocene compounds of formula (I):

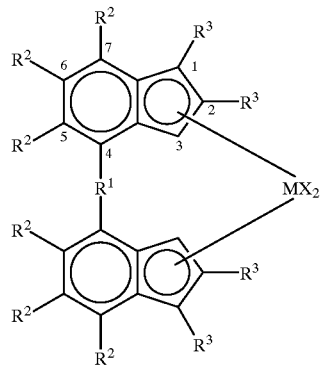

(I)

wherein
$R^1$ is a divalent group selected from $CR^4{}_2$, $C_2R^4{}_4$, $SiR^4{}_2$, $Si_2R^4{}_4$, $Ger^4{}_2$, $Ge_2R^4{}_4$, $R^4{}_2SiCR^4{}_2$, $NR^4$ and $PR^4$, in which the substituents $R^4$, which may be identical or different, are atoms of hydrogen, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals or $C_7$–$C_{20}$ aralkyl radicals and can contain atoms of Si or Ge, or, when $R^1$ is a $CR^4{}_2$, $C_2R^4{}_2$, $SiR^4{}_2$, $Si_2R^4{}_4$, $GeR^4{}_2$, $Ge_2R^4{}_4$ or $R^4{}_2SiCR^4{}_2$ group, two or four substituents $R^4$ can form one or two rings that have from 2 to 6 carbon atoms;

$R^2$ and $R^3$, which may be identical or different, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals or $C_7$–$C_{20}$ aralkyl radicals and can contain atoms of Si or Ge, and in addition two substituents $R^2$ or $R^3$ adjacent on the same indenyl can form a ring containing from 4 to 8 carbon atoms;

M is an atom of a transition metal selected from those belonging to groups 3, 4, 5 or 6 or to the lanthanides or the actinides in the Periodic Table of the Elements (new IUPAC version);

the substituents X, which may be identical or different, are hydrogen atoms, halogen atoms, R, OR, SR, $NR_2$ or $PR_2$ groups, wherein the substituents R are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals or $C_7$–$C_{20}$ aralkyl radicals and can contain atoms of Si or Ge.

According to another aspect of the present invention there is provided a compound of formula (II):

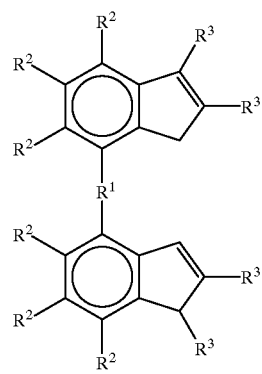

(II)

and its double bond isomers, wherein $R^1$, $R^2$ and $R^3$ are defined as above.

According to a further aspect of the present invention there are provided methods for the preparation of the above described compounds of formula (II).

According to a still further aspect of the present invention there is provided a catalyst for the polymerization of olefins, comprising the product of the reaction between:

(A) a metallocene compound of formula (I) as described above, and
(B) an alumoxane, or one or more compounds capable of forming an alkyl metallocene cation.

According to a still further aspect of the present invention there is provided a process for the polymerization of olefins comprising the reaction of polymerization of one or more olefinic monomers in the presence of a catalyst as described above.

DESCRIPTION OF THE PREFERRED EMBODIMENTS

The metallocene compounds according to the invention can exist in the racemic or meso isomeric form.

The divalent group $R^1$ is preferably a $C_2R^4_4$ group and, more preferably, it is a $(CH_2)_2$ group.

The transition metal M is preferably selected from titanium, zirconium and hafnium, zirconium being particularly preferred.

The substituents X are preferably chlorine atoms or methyl radicals.

A particularly interesting class of metallocenes according to the invention is that of the compounds of formula (I) in which the group $R^1$ is a $(CH_2)_2$ group, the substituents $R^2$ in the 5 and 6 positions and the substituents $R^3$ in the 3 positions are hydrogen atoms, the substituents $R^2$ in the 7 positions are different from hydrogen atoms, whereas the substituents $R^3$ in the 2 positions are preferably hydrogen atoms. Non-limiting examples of metallocene compounds belonging to the said class are:

rac- and meso-ethylenebis(7-methyl-4-indenyl)zirconium dichloride, rac- and meso-ethylenebis(2,7-dimethyl-4-indenyl) zirconium dichloride.

Another particularly interesting class of metallocenes according to the invention is that of the compounds of formula (I) in which the group $R^1$ is a $(CH_2)_2$ group, the substituents $R^2$ and the substituents $R^3$ in the 3 positions are hydrogen atoms, whereas the substituents $R^3$ in the 2 positions are different from hydrogen atoms. Non-limiting examples of metallocene compounds belonging to the said class are:

rac- and meso-ethylenebis(2-methyl-4-indenyl)zirconium dichloride.

A third particularly interesting class of metallocenes according to the invention is that of the compounds of formula (I) in which the group $R^1$ is a $(CH_2)_2$ group, the substituents $R^2$ in the 5 and 7 positions and the substituents $R^3$ in the 3 positions are hydrogen atoms, whereas the substituents $R^2$ in the 6 positions are different from hydrogen atoms. Non-limiting examples of metallocene compounds belonging to the said class are:

rac- and meso-ethylenebis(6-methyl-4-indenyl)zirconium dichloride, rac- and meso-ethylenebis(6-t-butyl-4-indenyl)zirconium dichloride, rac- and meso-ethylenebis(2,6-dimethyl-4-indenyl) zirconium dichloride, rac- and meso-ethylenebis(2-methyl-6-t-butyl-4-indenyl) zirconium dichloride.

A forth particularly interesting class of metallocenes according to the invention is that of the compounds of formula (I) in which the group $R^1$ is a $(CH_2)_2$ group, the substituents $R^2$ in the 7 positions and the substituents $R^3$ in the 3 positions are hydrogen atoms, the substituents $R^2$ in the 5 and 6 positions form an alkylene ring, and the substituents $R^3$ in the 2 positions are different from hydrogen atoms. Non-limiting examples of metallocene compounds belonging to the said class are:

rac- and meso-ethylenebis(2-methyl-5,6-cyclotetramethylene-4-indenyl)zirconium dichloride.

A fifth particularly interesting class of metallocenes according to the invention is that of the compounds of formula (I) in which the group $R^1$ is a $(CH_2)_2$ group, the substituents $R^3$ in the 3 positions are hydrogen atoms, and the substituents $R^2$ in the 6 and 7 positions form an alkylene ring. Non-limiting examples of metallocene compounds belonging to the said class are:

rac- and meso-ethylenebis(6,7-cyclotetramethylene-4-indenyl)zirconium dichloride, rac- and meso-ethylenebis(2-methyl-6,7-cyclotetramethylene-4-indenyl)zirconium dichloride, rac- and meso-ethylenebis(2,5-dimethyl-6,7-cyclotetramethylene-4-indenyl)zirconium dichloride.

A sixth particularly interesting class of metallocenes according to the invention is that of the compounds of formula (I) in which the substituents $R^3$ on each of the two cyclopentadienyl ring form an aromatic six-member ring, thus obtaining metallocene compounds bridged in the 1 position of the fluorenyl ring having the formula (Ia):

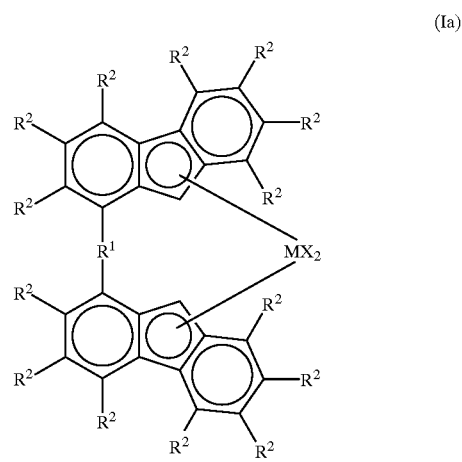

(Ia)

wherein $R^1$, $R^2$, M and X are defined as above. Preferably the $R^1$ group is a $(CH_2)_2$ group. These compounds are different from the known bridged bis-fluorenyl compounds in which the bridging group is linked to the fluorenyl rings in the 9 position. See e.g. European Patent Applications EP-A-524 624 and EP-A-604 908. Non-limiting examples of metallocene compounds belonging to the said class are:

rac- and meso-ethylenebis (1-fluorenyl)zirconium dichloride.

The aforementioned compounds of formula (II) are intermediate ligands that can be used for preparing the metallocene compounds of formula (I).

As in the case of the metallocene compounds of formula (I), the divalent group $R^1$ is preferably a $C_2R^4_4$ group and, more preferably, it is a $(CH_2)_2$ group.

Non-limiting examples of compounds of formula (II) according to the invention are:

1,2-bis(4-indenyl)ethane,
1,2-bis(7-methyl-4-indenyl)ethane,
1,2-bis(2-methyl-4-indenyl)ethane,
1,2-bis(6-methyl-4-indenyl)ethane,
1,2-bis(6-t-butyl-4-indenyl)ethane,
1,2-bis(2,6-dimethyl-4-indenyl)ethane,
1,2-bis(2,7-dimethyl-4-indenyl)ethane,
1,2-bis(2-methyl-6-t-butyl-4-indenyl)ethane,
1,2-bis(2-methyl-5,6-cyclotetramethylene-4-indenyl) ethane,
1,2-bis(6,7-cyclotetramethylene-4-indenyl)ethane,
1,2-bis(2-methyl-6,7-cyclotetramethylene-4-indenyl) ethane,
1,2-bis(2,5-dimethyl-6,7-cyclotetramethylene-4-indenyl) ethane, and
1,2-bis(1-fluorenyl)ethane.

The compounds of formula (II) can be prepared by different methods, depending on the presence and position of substituents on the indenyl-type moieties and on the $R^1$ group bridging them.

A particularly suitable process for preparing compounds of formula (II) in which $R^1$ is a $(CH_2)_2$ group and at least one substituent $R^2$ is different from a hydrogen atom, comprises the following steps:

(a) the Grignard coupling reaction of a benzyl halide of formula (III):

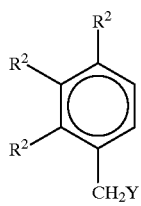

(III)

wherein Y is a halogen atom, preferably a chlorine atom, and the substituents $R^2$ have the meaning defined above, at least one substituent $R^2$ being different from a hydrogen atom, the said reaction being carried out in the presence of metallic magnesium, preferably under reflux and in the presence of an ether solvent such as tetrahydrofuran 13(THF), diethyl ether, 1,2-dimethoxyethane or dioxane;

(b) the reaction of the 1,2-diaryl-ethane of formula (IV):

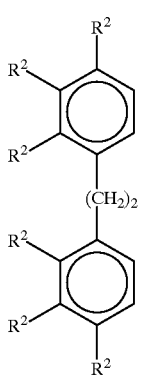

(IV)

obtained in step (a) with a compound of formula (V):

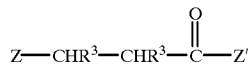

(V)

wherein Z and Z' are halogen atoms, preferably chlorine atoms, and the substituents $R^3$ have the meaning defined above, carried out in the presence of a Friedel-Crafts catalyst, such as aluminum chloride or another Lewis acid;

(c) the reaction of cyclization of the β-haloacyl derivatives obtained in step (b), carried out in the presence of a strong protic acid, such as sulphuric acid;

(d) the reaction of reduction of the diketones (4,4'-diindanonyl-1,2-ethane) obtained in step (c), carried out in the presence of a reducing agent such as $LiAlH_4$ or $NaBH_4$, preferably under reflux; and (e) the reaction of dehydration of the dialcohols obtained in step (d), carried out in an acidic environment.

Examples of compounds of formula (V) are the β-halogen-propionyl halides, in particular β-chloropropionyl chloride.

The benzyl halide of formula (III) and the compound of formula (V) are commercially available or can be prepared by known methods.

Depending on the position of the substituents $R^2$ that are different from a hydrogen atom in the benzyl halide of formula (III), the reaction of cyclization of step (c) can give rise to mixtures of diketones.

In the case when, in the benzyl halide of formula (III), the substituent $R^2$ para to the group $CH_2Y$ is different from a hydrogen atom, the various diketones that are obtained can all be converted to the desired end product. This is also true if the substituent $R^2$ in the para position is a hydrogen atom, but the substituent $R^2$ in the meta position is a hindering group, for example the tert-butyl group. In this case the positions a to the hindering group are inaccessible on account of the steric hindrance of the latter.

In all other cases, the desired 4,4'-diindanonyl-1,2-ethane diketones must be separated from the mixture of diketones that are obtained by the reaction of cyclization of step (c), for example by means of chromatographic columns.

The reactions of the other steps of the process are characterized by high yields and selectivity and therefore do not require burdensome steps of purification of the intermediates obtained.

According to one version of the said process, in step (b) the compound of formula (IV) can be reacted with a compound of formula (V'):

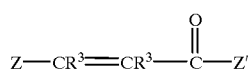

(V')

wherein Z, Z' and the substituents $R^3$ have the meanings defined above. In this way the cyclized product of step (c) is obtained directly. However, in this case the reaction must be conducted in controlled conditions of temperature (around −10° C.) to avoid secondary reactions of polymerization, and therefore complete cyclization is not achieved.

Another interesting process for preparing compounds of formula (II), particularly suitable to prepare those in which all the $R^2$ substituents are hydrogen atoms, comprises the following steps:

(a) the reaction of a compound of formula (VI):

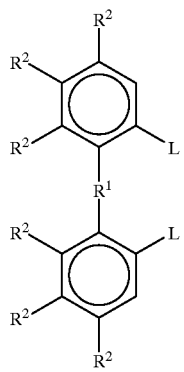

(VI)

wherein $R^2$ is defined as above and L is a leaving group such as a bromine atom a iodine atom, a tosilate or mesilate group, with a compound of formula (VII):

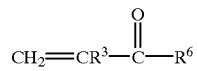

(VII)

wherein $R^3$ is defined as above except that it can not contain atoms of Si or Ge, and $R^6$ is a OH, OR, $NH_2$ or $NR_2$ group or a halogen atom, preferably being a OH group, said reaction being carried out in the presence of a base and of a palladium(II) salt;

(b) the reaction of hydrogenation of the unsaturated compound obtained in step (a), carried out in the presence of a hydrogenation catalyst such as Raney-nickel, platinum oxide, palladium, and of a hydrogenating agent such as hydrogen or hydrazine-hydrate;

(c) the reaction of cyclization of the compound obtained in step (b), carried out in the presence of a Friedel-Crafts catalyst, such as aluminum chloride or polyphosphoric acid;

(d) the reaction of reduction of the diketones (4,4'-diindanonyl-1,2-ethane) obtained in step (c), carried out in the presence of a reducing agent such as $LiAlH_4$ or $NaBH_4$, preferably under reflux;

(e) the reaction of dehydration of the dialcohols obtained in step (d), carried out in an acidic media.

The reaction of step (a) is generally carried out in an organic solvent, such as dimethylformamide, dimethylacetamide, piridine or triethylamine, dimethylformamide being the preferred, said organic solvent being optionally in admixture with water.

The reaction of step (a), especially when the leaving groups L in the compound of formula (VI) are different from iodine atoms, can conveniently be carried out in the presence of a tri-aryl-phosphine, such as tri-o-tolyl-phosphine.

The starting compound of formula (VII), if not commercially available, can be prepared by common organic synthetic methods. In the case in which the group $R^1$ is a $(CH_2)_2$ group, the starting compound of formula (VII) can suitably be prepared by the coupling reaction of a 2-substituted benzyl compound of formula (VIII):

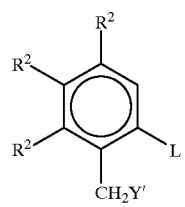

(VIII)

wherein $R^2$ and L are defined as above and Y' is a leaving group such as a halogen atom, a tosilate or a mesilate group, said reaction being carried out in the presence of a metal such as metallic magnesium, sodium, zinc etc., metallic magnesium being the preferred, in the presence of an organic solvent, preferably of the ether type such as tetrahydrofuran (THF), diethyl ether, 1,2-dimethoxyethane or dioxane.

A suitable way to prepare compounds of formula (II) wherein the substituents $R^3$ in the 1 position are different from hydrogen comprises the substitution of the step (d) in the above described processes with:

(d') the reaction of the diketones obtained in step (c) with organometallic compounds such as alkylmagnesium halides (Grignard reagents), alkyllithium compounds or sodium compounds.

The thus obtained compounds are then treated according to the procedure indicated under step (e) of the above described processes.

The metallocene compounds of formula (I) can be prepared by reaction of the corresponding ligands of formula (II) first with a compound capable of forming a delocalized anion on the cyclopentadienyl ring, and then with a compound of formula $MZ_4$ wherein M is defined as above and the substituents Z are halogen atoms.

Non-limiting examples of compounds of formula $MZ_4$ are titanium tetrachloride, zirconium tetrachloride, and hafnium tetrachloride.

In the case when at least one substituent X in the metallocene compound of formula (I) to be prepared is different from a halogen, it is necessary to substitute at least one substituent Z in the metallocene obtained with at least one substituent X different from a halogen.

The reaction of substitution of substituents Z with substituents X that are different from a halogen is carried out by methods that are in general use. For example, when the desired X substituents are alkyl groups, the metallocenes can be made to react with alkylmagnesium halides (Grignard reagents) or with alkyllithium compounds.

The metallocene compounds of the present invention can be used conveniently as catalytic components for the polymerization of olefins.

The alumoxane used in the catalyst according to the invention is considered to be a linear, branched or cyclic compound, containing at least one group of the type:

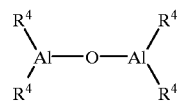

wherein the substituents $R^4$, which may be identical or different, are defined as for the substituents $R^2$ or are a group $—O—Al(R^4)_2$.

Examples of alumoxanes suitable for use according to the present invention are methylalumoxane (MAO), isobutyl-alumoxane (TIBAO) and 2,4,4-trimethylpentylaluminoxane (TIOAO). Mixtures of different alumoxanes can also be used.

Non-limiting examples of compounds capable of forming an alkyl metallocene cation are compounds of formula $Y^+Z^-$, wherein $Y^+$ is a Bronsted acid capable of donating a proton and of reacting irreversibly with a substituent X of the compound of formula (I), and $Z^-$ is a compatible anion which does not coordinate, which is capable of stabilizing the active catalytic species originating from the reaction of the two compounds, and which is sufficiently labile to be able to be displaced from an olefinic substrate. The $Z^-$ anion preferably comprises one or more boron atoms. More preferably, the $Z^-$ anion is an anion of formula $BAr_4(^-)$, wherein the Ar substituents, which may be identical or different, are aryl radicals such as phenyl, pentafluorophenyl, bis-(trifluoromethyl)phenyl. Tetrakis-pentafluorophenyl borate is particularly preferred. Moreover, compounds of formula $BAr_3$ can be used conveniently.

In the catalyst used in the process of the invention, both the metallocene compound of formula (I) and the alumoxane can be present as the product of reaction with an organometallic compound of aluminum of formula $AlR^5{}_3$ or $Al_2R^5{}_6$, in which the substituents $R^5$, which may be identical or different, are defined as for the substituents $R^2$ or are halogen atoms.

Non-limiting examples of aluminum compounds of formula $AlR^5{}_3$ or $Al_2R^5{}_6$ are:

$Al(Me)_3$, $Al(Et)_3$, $AlH(Et)_2$, $Al(iBu)_3$, $AlH(iBu)_2$, $Al(iHx)_3$, $Al(C_6H_5)_3$, $Al(CH_2C_6H_5)_3$, $Al(CH_2CMe_3)_3$, $Al(CH_2SiMe_3)_3$, $Al(Me)_2iBu$, $Al(Me)_2Et$, $AlMe(Et)_2$, $AlMe(iBu)_2$, $Al(Me)_2iBu$, $Al(Me)_2Cl$, $Al(Et)_2Cl$, $AlEtCl_2$, $Al_2(Et)_3Cl_3$, wherein Me=methyl, Et=ethyl, iBu=isobutyl, iHx=isohexyl.

Of the abovementioned compounds of aluminum, trimethylaluminum (TMA) and triisobutylaluminum (TIBAL) are preferred.

The catalysts of the present invention can also be used on inert supports. This is achieved by depositing the metallocene compound (A), or the product of its reaction with component (B), or component (B) and then the metallocene compound (A), on inert supports such as silica, alumina, styrene-divinylbenzene copolymers or polyethylene.

The solid compound thus obtained, in combination with further addition of alkyl aluminum compound either untreated or pre-reacted with water, if necessary, is used advantageously in gas-phase polymerization.

In the process for the polymerization of olefins according to the invention, preferred olefinic monomers are ethylene, α-olefins, such as propylene and 1-butene, cycloolefins and conjugated diolefins.

The catalysts according to the invention can be used advantageously in the reactions of homopolymerization of ethylene or of α-olefins such as propylene and 1-butene, or in reactions of copolymerization of ethylene with α-olefins such as propylene and 1-butene, or in reactions of copolymerization between α-olefins such as propylene and 1-butene.

In particular, with the catalysts of the invention it is possible to prepare elastomeric copolymers of ethylene with α-olefins of formula $CH_2=CHR$, wherein R is an alkyl radical containing from 1 to 10 carbon atoms, if necessary containing minor proportions of units derived from polyenes.

The saturated elastomeric copolymers that can be obtained with the catalysts of the present invention contain from 15% to 85% in moles of ethylenic units, the complement to 100 consisting of units of one or more α-olefins and/or of a nonconjugated diolefin capable of cyclopolymerizing.

The unsaturated elastomeric copolymers also contain, along with the units derived from the polymerization of ethylene and of the α-olefins, minor proportions of unsaturated units derived from the copolymerization of one or more polyenes. The content of unsaturated units can vary over a wide range. Terpolymers of interest are those which contain from 0.1 to 20% by weight, preferably from 0.3 to 10% by weight, more preferably from 0.5 to 5% by weight of unsaturated units.

The elastomeric copolymers of ethylene that can be obtained with the catalysts of the invention are characterized by valuable properties, such as low ash content and uniform distribution of the comonomers in the copolymer chain.

The α-olefins that can be used include, for example, propylene, 1-butene, 4-methyl-1-pentene. The preferred α-olefin is propylene.

1,5-Hexadiene, 1,6-heptadiene, and 2-methyl-1.5-hexadiene can be used as non-conjugated diolefins capable of cyclopolymerizing.

The following can be used as polyenes capable of giving unsaturated units:

conjugated dienes, for example butadiene and isoprene;

nonconjugated linear dienes, for example 1,4-hexadiene trans, 1,4-hexadiene cis, 6-methyl-1,5-heptadiene, 3,7-dimethyl-1,6-octadiene, 11-methyl-1,10-dodecadiene;

monocyclic diolefins, for example cis-1,5-cyclooctadiene and 5-methyl-1,5-cyclooctadiene;

bicyclic diolefins, for example 4,5,8,9-tetrahydroindene and 6 and/or 7-methyl-4,5,8,9-tetrahydroindene;

alkenyl or alkylidene norbornenes, for example 5-ethylidene-2-norbornene, 5-isopropylidene-2-norbornene, exo-5-isopropenyl-2-norbornene;

polycyclic diolefins, for example dicyclopentadiene, tricyclo-$[6.2.1.0^{2.7}]$-4,9-undecadiene and its 4-methyl derivative.

Preferred polyenes are 5-ethylidene-2-norbornene (ENB), 1,4-hexadiene trans and 1,4-hexadiene cis, 5-ethylidene-2-norbornene being particularly preferred.

The process of polymerizing the olefins according to the invention can be carried out in the liquid phase, in the presence or absence of an inert hydrocarbon solvent, or in the gas phase. The hydrocarbon solvent can be either aromatic, such as toluene, or aliphatic, such as propane, hexane, heptane, isobutane, and cyclohexane.

The polymerization temperature is generally between −100° C. and +80° C., and more particularly between −50° C. and +50° C. The lower the polymerization temperature, the higher are the molecular weights of the polymers obtained.

The molecular weight of the polymers can, more-over, be varied by changing the type or the concentration of the catalytic components or by using molecular weight regulators, for example hydrogen.

The molecular weight distribution can be varied by using mixtures of different metallocene compounds, or by carrying out the polymerization in several steps that differ with respect to the temperatures of polymerization and/or the concentrations of molecular weight regulator.

The polymerization yields depend on the purity of the metallocene component of the catalyst. Accordingly, the metallocene compounds obtained by the process of the invention can be used as they are, or they can undergo purification treatments.

The components of the catalyst can be brought into contact with each other prior to polymerization. The duration of contact is generally between 1 and 60 minutes, preferably between 5 and 20 minutes. The precontact concentrations for the metallocene component (A) are between $10^{-2}$ and $10^{-8}$ mol/l, whereas for component (B) they are between 10 and $10^{-3}$ mol/l. Precontact is generally effected in the presence of a hydrocarbon solvent and, if necessary, of small amounts of monomer.

The following examples are given by way of illustration of the invention and are non-limiting.

CHARACTERIZATIONS

The ligands and metallocenes of Examples 1–3 were characterized by $^1$H-NMR analyses with a Bruker AC200 instrument at 200.133 MHz, using $CDCl_3$ as solvent, at room temperature. The spectra were recorded with a 150 pulse and a relaxation delay of 1 second.

The ligands and metallocenes of Examples 14–25 were characterized by NMR analyses with a Varian Gemini 300 instrument ($^1$H-NMR at 300 MHz, $^{13}$C-NMR at 75.4 MHz) or with a Varian XL200 instrument ($^1$H-NMR at 200 MHz, $^{13}$C-NMR at 50.1 MHz). The solvents are as indicated and the measurements were performed at 20° C.

$^{13}$C-NMR analyses of the copolymer of Example 7 were effected with a Bruker AC200 instrument at 200.133 MHz, at a temperature of 120° C., on samples in solution at 8% by weight in $C_2D_2Cl_4$. The spectra were recorded with a 90° pulse, a relaxation delay of 12 seconds and a number of scans of 2000–2500.

The content of ethylenic units in the ethylene/propylene elastomeric copolymers was determined by means of IR analysis, whereas the content of ethylenic units and unsaturated units in the ethylene/propylene/ENB terpolymers was determined by $^1$H-NMR analysis.

The polymers of Examples 26–43 were characterized by $^{13}$C-NMR analyses with a Bruker 500 instrument at 125.4 MHz. The samples were dissolved in 1,2,4-triclorobenzene with some 1,4-$C_6D_4Cl_2$ added as lock. The measurements were in 5 mm NMR tobes at 130° C. with a 70° pulse and a relaxation delay of 15 seconds.

The intrinsic viscosity [η] of the polymers of Examples 4–13 was measured in tetralin at 135° C.

The limiting viscosity number [LVN] of the polymers of Examples 26–39 was measured at 135° C. in decalin which was inhibited with ionol (1 g/L).

PREPARATION OF LIGANDS AND METALLOCENES

All the operations were performed in an anhydrous nitrogen atmosphere, using the conventional techniques for the handling of compounds that are sensitive to air.

POLYMERIZATIONS

MODIFIED METHYLALUMOXANE (M-MAO)

A commercial product (ALBEMARLE) was used as received, in solution (62 g Al/l) in isopar C.

TRIS-(2,4,4-TRIMETHYLPENTYL)ALUMINUM (TIOA)

This was prepared according to the method described in Liebigs Ann. Chem. Bd. 629, Ziegler et al. "Aluminumtrialkyls and dialkylaluminum hydrides from aluminum isobutyl compounds" pp. 14–19.

EXAMPLE 1

1,2-bis(7-methyl-4-indenyl)ethane (a) Synthesis of 1,2-di-p-tolylethane 200 ml of anhydrous tetrahydrofuran (THF), 3.35 g (0.138 mol) of Mg turnings and a crystal of $I_2$ were placed in a 500-ml three-necked round-bottomed flask equipped with a 100-ml dropping funnel, thermometer and reflux condenser. Then a solution of 35.15 g (0.25 mol) of α-chloro-p-xylene in 50 ml of anhydrous THF was added drop by drop. Heating was required to start the reaction, then self-heating was observed. After 3 hours, all of the Mg had dissolved. The reaction mixture was kept under reflux for 3 hours, then left to rest for one night. All the THF was evaporated at reduced pressure and the residue was treated with a mixture of 150 ml of hexane and 150 ml of 10% HCl. The organic phase was separated, washed with aqueous NaCl (3 times) and dried over $Na_2SO_4$. After evaporating the solvent, white crystals were isolated, and these were dried under vacuum at 70° C. 24.3 g of 1,2-di-p-tolylethane was obtained (yield: 92.4%).

$^1$H-NMR ($CDCl_3$), δ (ppm): 2.35 (6H, s, 2 —$CH_3$), 4.65 (4H, s, 2 —$CH_2$—), 7.22 (8H, q, arom.).

(b) Synthesis of 3,3'-di-(β-chloropropiophenone)-4,4'-dimethyl-1,2-ethane, 2,3'-di-(β-chloropropiophenone)-4,4'-dimethyl-1,2-ethane and 2,2'-di-(62 -chloropropiophenone)-4,4'-dimethyl-1,2-ethane 33.2 g (0.109 mol) of $AlCl_3$ and 90 ml of $CH_2Cl_2$ were placed in a 250-ml three-necked round-bottomed flask equipped with a 100-ml dropping funnel, thermometer and reflux condenser. The suspension obtained was cooled to 0° C. and 23 ml of β-chloropropionyl chloride was added dropwise. The reaction mixture was stirred for 1 hour at –5° C., then a solution of 22.3 g (0.106 mol) of p-tolylethane in 50 ml of $CH_2Cl_2$ was added dropwise. The suspension obtained was stirred for 2 hours, maintaining the temperature at 0° C. The course of reaction was followed by thin-layer chromatography (TLC), using a hexane/ethyl acetate 7/3 mixture as eluent. The reaction was stopped with ice and HCl 37%. The aqueous phase was extracted with $CH_2Cl_2$. The combined organic phases were washed with a saturated aqueous solution of NaCl (50 ml), dried over $Na_2SO_4$, filtered, and the solvent was then removed under vacuum. 37.5 g of the mixture of diketones was obtained as a pale yellow solid (yield: 90.5%).

$^1$H-NMR ($CDCl_3$); δ (ppm): 2.5 (6H, s, —2$CH_3$), 2.9 (4H, s, 2 —$CH_2$— bridges), 3.3 (4H, t, 2 —$CH_2$—CO—), 3.9 (4H, t, 2 —$CH_2$—Cl), 7.3 (4H, s, arom.), 7.4 (2H, s, arom.).

(c) Synthesis of 7,7'-dimethyl-4,4'-diindanonyl-1,2-ethane, 4,7'-dimethyl-4',7-diindanonyl-1,2-ethane and 4,4'-dimethyl-7,7'-diindanonyl-1,2-ethane 210 ml of $CH_2Cl_2$, 36 g of the mixture of diketones obtained in step (b) and 10 mg of $(C_4H_9)_4NHSO_4$ were placed in a 250-ml three-necked round-bottomed flask equipped with a 100-ml dropping funnel, thermometer and reflux condenser. Then 106 ml of $H_2SO_4$ 96% was added dropwise, and the reaction mixture was kept under reflux for 4 hours. The course of the reaction was followed by TLC, using a 7/3 hexane/ethyl acetate mixture as eluent. The mixture was then cooled to room temperature and slowly poured over ice. The solution was neutralized with NaOH and extracted with $CH_2Cl_2$. The combined organic phases were washed with a saturated aqueous solution of NaCl (100 ml), dried over $Na_2SO_4$, filtered, and the solvent was then removed under vacuum. 27.8 g of the mixture of diketones was obtained as a white solid (yield: 95%).

$^1$H-NMR ($CDCl_3$); δ (ppm): 2.5–2.8 (6+4H, s+m, 2 —$CH_3$+2 —$CH_2$—CO—), 2.8–3.15 (4+4H, s+m, —$CH_2$— bridge+ —$CH_2$—5 ring), 7.05 (2H, d, arom.), 7.2 (2H, d, arom.).

(d) Synthesis of 7,7'-dimethyl-4,4'-diindanolyl-1,2-ethane, 4,7'-dimethyl-4',7-diindanolyl-1,2-ethane and 4,4'-dimethyl-7,7'-diindanolyl-1,2-ethane 3.2 g of LiAlH$_4$ and 240 ml of anhydrous THF were placed in a 500-ml three-necked round-bottomed flask equipped with a 250-ml dropping funnel, thermometer and reflux condenser. Then a solution containing 27 g (0.085 mol) of the mixture of diketones obtained in step (c) in 160 ml of anhydrous THF was added at room temperature over the course of 40 minutes. After the addition, the reaction mixture was kept under reflux for 5 hours. The course of reaction was followed by TLC, using a 7/3 hexane/ethyl acetate mixture as eluent. The suspension was cooled to room temperature, then 50 ml of ethyl acetate followed by 50 ml of water were slowly added. The THF was evaporated by rotavac. The residue was filtered in a Büchner on a layer of Celite to facilitate filtration. The aqueous phase was extracted with CH$_2$Cl$_2$. The combined organic phases were dried over Na$_2$SO$_4$, filtered, and the solvent was removed under vacuum. 24.7 g of the mixture of dialcohols was obtained (yield: 90%).

$^1$H-NMR (CDCl$_3$); δ (ppm): 1.5–2.5 (12H, m, 2 —CH$_3$—+2 —CH$_2$— non-benz. +2 —OH), 2.5–3.3 (8H, m, 2 bridges—CH$_2$—+2 —CH$_2$—benz. ring at 5), 5.25 (2H, m, 2 —CH— adjacent to —OH), 6.9–7.15 (4H, m, arom.).

(e) Synthesis of 4,4'-dimethyl-7,7'-diindenyl-1,2-ethane, 7,7'-dimethyl-4,4'-diindenyl-1,2-ethane and 4,7'-dimethyl-4',7-diindenyl-1,2-ethane 450 ml of benzene and 150 mg of p-toluenesulphonic acid were placed in a 1-litre round-bottomed flask equipped with a Dean-Stark trap. The solution obtained was kept under ref lux for 2 hours in order to eliminate the water by azeotropic distillation. Then 14.5 g of the mixture of dialcohols obtained in step (d) was added, and the solution obtained was kept under reflux for 1 hour, monitoring the amount of water formed. The course of reaction was followed by TLC, using a 7/3 hexane/ethyl acetate mixture as eluent. After cooling to room temperature, the reaction mixture was washed with a saturated solution of NaHCO$_3$ (150 ml), then with H$_2$O (100 ml), dried over Na$_2$SO$_4$, and the solvent was evaporated under vacuum. 12.3 g of the mixture of bisindenyl derivatives was obtained, with purity of 78% (GC). The product was purified by means of a chromatographic column on silica gel, using a 7/3 hexane/ethyl acetate mixture as eluent. 5.7 g of the first fraction eluted was obtained, with purity of 95.5 (GC). This fraction was used for preparing the metallocene.

$^1$H-NMR (CDCl$_3$); δ (ppm): 2.5 (6H, s, 2 —CH$_3$), 3.05 (4H, s, 2 —CH$_2$— bridges), 3.35 (4H, s, 2 —CH$_2$— ring at 5), 6.6 (1H, m, H2 indene), 7.0–7.2 (2+1H, m, arom. +H3 indene).

EXAMPLE 2 rac-ethylenebis(7-methyl-4-indenyl)zirconium Dichloride

A solution of 2.8 g of bis(7-methyl-4-indenyl)ethane obtained in Example 1 in 50 ml of THF was cooled to its melting point in a bath of liquid N$_2$. 15 ml of a 1.6 M solution of BuLi in hexane was added by means of a steel capillary. A light-brown suspension is obtained—this is brought back to room temperature and stirred for 2 hours. Separately, 3.5 g of ZrCl$_4$(THF)$_2$ is dissolved in 65 ml of THF. The two mixtures are fed simultaneously (3 ml every 15 min, total time for addition approx. 5 hours) into a 250-ml round-bottomed flask containing 40 ml of THF. A brown solution was obtained, which turned yellow in time. At the end of addition the solution was stirred for 21 hours at room temperature. In this way a yellowish-brown solution was obtained, to which, after concentration in vacuum to a small volume, 40 ml of Et$_2$O was added. The suspension thus obtained was filtered, and the residue was extracted with Et$_2$O until the washwater was colourless. The ether fractions were combined and dried, obtaining 1.9 g of yellow powder. This powder was then extracted with CH$_2$Cl$_2$ continuously (Soxhlet) and the extract was dried. 1.69 g of a paste-like solid was obtained; this was suspended in 10 ml of toluene, filtered and the filtrate was stored at −20° C. After some days, 0.73 g of a yellow solid was recovered by filtration. $^1$H-NMR analysis demonstrates that the desired product has formed.

$^1$H-NMR (200 MHz, CDCl$_3$, δ (ppm) from TMS): 7.25–7.0 (4H), 6.8–6.6 (m, 4H), 4.5–4.4 (m, 2H), 3.5–2.9 (m, 4H), 2.6 (s, 6H).

EXAMPLE 3 rac-ethylenebis(7-methyl-4-indenyl)zirconium Dichloride

A solution of 2.8 g of bis(7-methyl-4-indenyl)ethane obtained in Example 1 in 50 ml of THF was added in small portions to a suspension of 0.83 g of KH in 30 ml of THF. It is noted that gases are evolved. At the end of addition, the suspension thus obtained was stirred for 2 hours at room temperature, obtaining a dark green solution which was filtered to remove the unreacted excess KH. This solution was added, via a dropping funnel, to a solution of 3.52 g of ZrCl$_4$(THF)$_2$ dissolved in 50 ml of THF. A yellowish-brown suspension was obtained, and was stirred for 18 hours at room temperature. In this way a yellow suspension was obtained, which was dried, obtaining a yellowish-orange powder, which was then extracted with Et$_2$O until the washwater was colourless. The ether extract was dried, obtaining a yellow paste-like solid which was then suspended in 50 ml of CR$_2$Cl$_2$, filtered and dried and the residue was washed with 30 ml of hexane at 35° C., suspended in 10 ml of toluene, and finally filtered. 0.39 g of solid product was recovered by filtration. $^1$H-NMR analysis shows that the desired product is formed as a mixture of two conformational isomers.

EXAMPLE 4

Polymerization of Propylene

A 1-litre jacketed steel Büchi autoclave equipped with a magnetic-drive helical stirrer, 35 cm$^3$ barrel and heat resistance, connected to a thermostat for temperature control, washed with a solution of Ali-Bu$_3$ in hexane and then dried at 60° C. in a stream of nitrogen, was loaded with 400 g of propylene. The autoclave was then thermostated at 48° C.

The catalyst/cocatalyst mixture was prepared by dissolving 1.0 mg of the metallocene prepared in Example 2 in toluene, adding M-MAO (4.48 mmol Al), thus obtaining a solution which was stirred for 10 minutes at room temperature and was then injected into the autoclave from the barrel by means of propylene pressure. The temperature was raised quickly to 50° C. and polymerization was carried out at constant temperature for one hour. The reaction was stopped by introducing CO into the reactor. The unreacted monomers were vented and the polymer obtained was desiccated under vacuum at 60° C. 1.1 g of polypropylene was obtained in this way.

EXAMPLE 5

Polymerization of Propylene

The procedure described in Example 4 was followed, except that 4 mg of metallocene was used. In this way, 4.3 g of polypropylene was obtained, and this was submitted to exhaustive extraction in a Kumagawa with diethyl ether for 8 hours, and then with n-hexane for 16 hours. No insoluble product remained. The following two fractions were obtained:

fraction A (35% by weight) soluble in $Et_2O$, possessing intrinsic viscosity $\eta=0.15$ dl/g, melting point $T_m=75.1°$ C. and enthalpy of fusion $\Delta H_f=29$ J/g and 56.2% of mmmm pentads;

fraction B (65% by weight) insoluble in $Et_2O$ and soluble in n-hexane, possessing $\eta=0.24$ dl/g, $T_m=100.6°$ C., $\Delta H_f=50$ J/g and 63.5% of mmmm pentads.

EXAMPLE 6

Copolymerization of Propylene with Ethylene

The procedure described in Example 5 was followed, except that a pressure of 1 $kg/cm^3$ of ethylene was introduced into the autoclave, and this was kept constant throughout the reaction. 36 g of a transparent, amorphous copolymer was obtained, which had intrinsic viscosity of 0.76 dl/g, 39.3% by weight of ethylene units and 60.7% by weight of propylene units.

EXAMPLE 7

Preparation of $C_2/C_3$ Elastomeric Copolymers

A 100-ml reactor, equipped with magnetic stirrer, temperature and pressure gauges, and feed lines for the monomers and nitrogen, was supplied at room temperature with 45 ml of toluene and 4.5 mmol of TIOA. Then 2.25 mmol of water was added by means of a syringe and it was left for precontact for 20 minutes. The system was saturated with an ethylene/propylene mixture in the ratio 20:80 by weight at ambient pressure. The polymerization reaction was initiated by adding 4.02 mg (0.009 mmol) of the metallocene of Example 3 in a toluene solution and the pressure of the ethylene/propylene mixture was adjusted to 2 bar. After 30 minutes the reaction was stopped by degassing of the monomers and introduction of 2 ml of methanol into the reactor. The polymerization solution was poured into methanol containing HCl, filtered and then dried thoroughly under vacuum. The polymerization conditions and the data relating to characterization of the copolymer obtained are reported in Table 1.

$^{13}$C-NMR analysis of the copolymer: $r_1xr_2=0.8$; PPP/P= 23%; iso value=73%.

EXAMPLE 8

Preparation of $C_2/C_3$/ENB Elastomeric Terpolymers

The procedure described in Example 7 was followed, except that 2.5 ml (18.6 mmol) of 5-ethylidene-2-norbornene (ENB) was introduced, together with toluene and TIOA, into the reactor. The polymerization conditions and the data relating to characterization of the terpolymer obtained are reported in Table 1.

EXAMPLE 9

Preparation of $C_2/C_3$ Elastomeric Copolymers 1326 g of hexane and the quantities of ethylene and propylene stated in Table 1 were introduced at room temperature into a 4.25-litre steel autoclave equipped with a mechanical stirrer, manometer, temperature gauge, catalyst charging system, feed lines for the monomers and a jacket for thermostatic control, the autoclave having been cleaned beforehand by rinsing with propylene at 70° C. The catalyst solution, prepared by adding a 2.3 M solution of M-MAO to the metallocene of Example 3, was injected into the autoclave via a steel barrel, under ethylene pressure, at a temperature about 2° C. below the polymerization temperature. The temperature was then raised over a period of approximately 2 minutes to the value required for polymerization, and was kept constant throughout polymerization. The pressure was kept constant by supplying an ethylene/propylene mixture in a ratio of approx. 60/40 by weight. The reaction was then interrupted by rapid degassing of the monomers, and the polymer obtained was dried in a stove at 60° C. in vacuum. The conditions of polymerization and data relating to characterization of the copolymer obtained are given in Table 1.

EXAMPLE 10

Preparation of $C_2/C_3$/ENB Elastomeric Terpolymers

The procedure described in Example 9 was followed, except that 6.5 ml of ENB was fed into the reactor, in addition to hexane, ethylene and propylene. Furthermore, 1 ml of ENB for every 5 g of ethylene was fed into the reactor during polymerization. The conditions of polymerization and the data relating to characterization of the terpolymer obtained are shown in Table 1.

EXAMPLES 11–13

Preparation of $C_2/C_3$ Elastomeric Copolymers

The quantities of ethylene, propylene, hexane and water stated in Table 1 were fed at room temperature into a 4.25-litre steel autoclave, equipped with a mechanical stirrer, manometer, temperature gauge, catalyst charging system, lines for feeding in the monomers and a jacket for thermostatic control, the autoclave having been cleaned beforehand by rinsing with propylene at 70° C. The catalyst solution, prepared by adding a 1 M solution of TIOA to the metallocene of Example 3, was injected into the autoclave via a steel barrel, under ethylene pressure, at a temperature approx. 2° C. below the polymerization temperature. The temperature was then raised over a period of about 2 minutes to the value required for polymerization, and was kept constant throughout polymerization. The pressure was kept constant by supplying an ethylene/propylene mixture in a ratio equal to the composition of the polymer obtained. The reaction was then interrupted by rapid degassing of the monomers, and the polymer obtained was dried in a stove at 60° C. in a nitrogen stream. The conditions of polymerization and the data relating to characterization of the terpolymer obtained are shown in Table 1.

EXAMPLE 14

1,2-bis(7-methyl-4-indenyl)ethane (A) synthesis of 1,2-di-p-tolylethane

To a suspension of 9.55 g Mg (0.39 mol) and a crystal of $I_2$ in 500 ml anhydrous THF was added a solution of 100 g p-methylbenzylchloride (0.71 mol) in 150 ml anhydrous THF under an inert atmosphere in 30 minutes. The exothermic reaction caused the mixture to reflux. Subsequently the reaction mixture was refluxed for 3 hours. The solvent was evaporated under reduced pressure and the remaining white solid was treated with 400 ml pentane and 400 ml aqueous 10% HCl. The organic layer was extracted with 150 ml saturated NaCl (2 times) and dried with $MgSO_4$. The solvent was evaporated under reduced pressure giving 69.8 g (0.33 mol, 93%) product as a white powder.

$^1$H NMR ($CDCl_3$, 300 MHz): δ 7.25 (s, 8H, aromatic), 3.03 (s, 4H, —$CH_2$—), 2.49 (s, 6H, $CH_3$) ppm. $^{13}$C NMR ($CDCl_3$, 75 MHz): δ 21.0 (C1), 37.6 (C6), 128.3 (C4), 129.0 (C3), 135.2 (C2), 138.8 (C5) ppm.

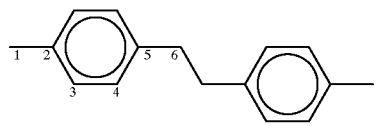

(B) Synthesis of 3,3'-di-(β-chloropropiophenone)-4,4'-dimethyl-1,2-ethane, 2,3'-di-(β-chloropropiophenone)-4,4'-dimethyl-1,2-ethane and 2,2'-di-(β-chloropropiophenone)-4,4'-dimethyl-1,2-ethane To a suspension of 51.3 g (0.38 mol) $AlCl_3$ in 150 ml anhydrous $CH_2Cl_2$ was added 47.3 g (0.37 mol) 3-chloropropionylchloride at 0° C. in 5 minutes. After stirring the reaction mixture at 0° C. for 30 minutes a solution of 34.5 g of 1,2-di-p-tolylethane in 80 ml anhydrous $CH_2Cl_2$ was added dropwise over a period of 40 minutes at 0° C. Upon addition the colour changed from yellow to dark red. The reaction mixture was stirred for 2 hours at 0° C., subsequently poured onto ice and acidified with 37% HCl. The aqueous layer was extracted with an extra 150 ml $CH_2Cl_2$. The combined organic layers were extracted with 150 ml saturated aqueous NaCl (3 times) and dried over $MgSO_4$. The solvent was evaporated in vacuo giving a sticky solid. Washing the solid with cold pentane gives a 56.1 g (0.14 mol, 86.4%) off white powder. According to NMR three isomers are formed, two symmetrical (1 and 2) and one asymmetric (3):

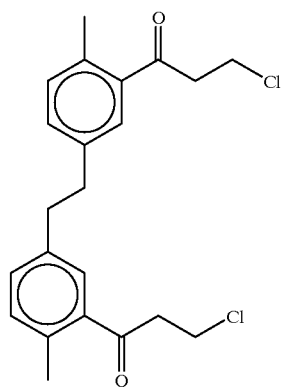

1

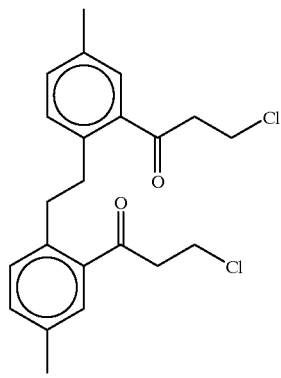

2

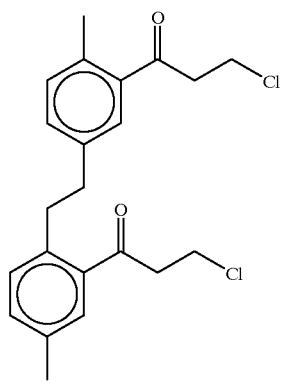

3

According to $^1$H NMR isomer 1 is formed for 46%, isomer 2 for 1.8% and isomer 3 for 52.2%.

$^1$H NMR ($CDCl_3$, 300 MHz):

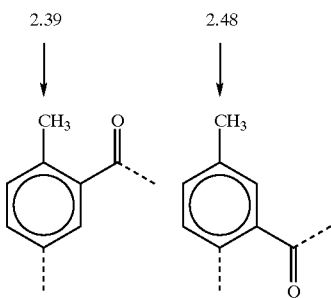

The methyl group gives two signals because of the influence of the position of the propionyl group. The propionyl group ortho to the methyl gives a singlet at 2.39 ppm, meta gives a signal at 2.48 ppm. The protons in the bridge for the symmetrical isomers (1 and 2) are giving a singlet, the asymmetrical isomer (3) gives two multiplets.

δ 7.1–7.45 (m, 6H, aromatic), 3.87 (m, 4H, —$CH_2CH_2Cl$), 3.29 (m, 4H, —$CH_2CH_2Cl$), 3.09 (m, 2H, $CH_2$ bridge asymm.), 2.94 (s, 4H, $CH_2$ bridge symm.), 2.89 (m, 2H, $CH_2$ bridge asymm.), 2.48 (s, 3H, $CH_3$), 2.39 (s, 3H, $CH_3$). $^{13}$C NMR ($CDCl_3$, 75 MHz):

Because of the three isomers, the $^{13}$C NMR data looks rather complex; much of the signals come in pairs of three.

δ 20.78 ($CH_3$), 20.85 ($CH_3$), 20.90 ($CH_3$), 35.52 ($CH_2$ bridge), 37.07 ($CH_2$ bridge), 37.52 ($CH_2$ bridge), 38.89

(—CH₂C₂Cl), 38.94 (—CH₂CH₂Cl), 39.02 (—CH₂CH₂Cl), 43.69 (—CH₂CH₂Cl), 43.74 (—CH₂CH₂Cl), 43.83 (—C₂CH₂Cl), 128.73 (arom. CH), 128.98 (arom. CH), 129.16 (arom. CH), 131.53 (arom. CH), 131.88 (arom. CH), 132.02 (arom. CH), 132.07 (arom. CH), 132.12 (arom. CH), 132.47 (arom. CH), 135.83 (q-C), 135.95 (q-C), 136.08 (q-C), 136.66 (q-C), 136.94 (q-C), 137.08 (q-C), 138.46 (q-C), 138.53 (q-C), 139.33 (q-C) ppm.

(C) Synthesis of 7,7'-dimethyl-4,4'-diindanonyl-1,2-ethane, 4,7'-dimethyl-4',7-diindanonyl-1,2-ethane and 4,4'-dimethyl-7,7'-diindanonyl-1,2-ethane To a suspension of 56.1 g (0.14 mol) of the product obtained in step (B) and 16 mg Bu₄NHSO₄ in 330 ml CH₂Cl₂ was added 165 ml 96% H₂SO₄ at room temperature on which the colour changed to dark red. The two phase reaction mixture was refluxed for 4 hours and after cooling poured onto ice. Subsequently the mixture was carefully neutralised with NaOH pellets and extracted with CH₂Cl₂. The combined organic layers where dried over MgSO₄. The solvent was evaporated under reduced pressure yielding 42.5 g (0.13 mol, 94%) of the bridged indanone as a beige powder.

¹H NMR (CDCl₃, 300 MHz): δ 6.96–7.36 (m, 4H, J=7.5 Hz, arom.), 3.24–3.32 (m, CH₂), 2.84–3.08 (m, CH₂), 2.92 (s, CH₂, bridge), 2.60–2.72 (m, CH₂), 2.60 (s, CH₃), 2.32 (s, CH₃) ppm.

Because of the possible isomers, the ¹H spectrum gives not only singlet signals for the bridging protons but also some multiplet signals in the case of the asymmetric isomer.

¹³C NMR (CDCl₃, 75 MHz):

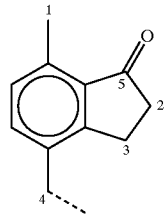

δ 17.41 (CH₃, C1), 17.99 (CH₃, C1), 23.81 (CH₂, C3), 24.30 (CH₂, C3), 32.05 (CH₂, C4), 32.32 (CH₂, C4), 33.15 (CH₂, C4), 36.53 (CH₂, C2), 36.61 (CH₂, C2), 36.71 (CH₂, C2), 128.56 (arom. CH), 129.26 (arom. CH), 129.46 (arom. CH), 133.57 (arom. CH), 133.65 (q-C), 133.93 (arom. CH), 134.19 (q-C), 134.34 (q-C), 134.57 (arom. CH), 135.99 (q-C), 136.21 (q-C), 136.68 (q-C), 136.74 (q-C), 139.34 (q-C), 154.04 (q-C), 154.52 (q-C), 155.20 (q-C), 207.96 (C=O, C5), 208.50 (C=O, C5) ppm.

(D) Synthesis of 4,4'-dimethyl-7,7'-diindenyl-1,2-ethane, 7,7'-dimethyl-4,4'-diindenyl-1,2-ethane and 4,7'-dimethyl-4',7-diindenyl-1,2-ethane To a suspension of 28.3 g (86.6 mmol) of the product obtained in step (C) in 500 ml THF/methanol (2:1) was added portionwise 11.3 g (300 mmol) NaBH₄ at 0° C. After addition (10 minutes) the reaction mixture was allowed to warm to room temperature and was stirred overnight. The release of H₂ was observed and the reaction mixture changed to a clear yellow solution. Subsequently, the reaction mixture was poured onto ice, acidified to pH 1 and extracted with ether. The combined organic layers were extracted with extra aqueous 10% HCl (2 times) to complete the dehydration and dried over MgSO₄. The solvent was evaporated and the sticky white product was washed with pentane. The product was isolated as a off-white powder, 11.5 g (40.2 mmol, 46.4%).

¹H NMR (CDCl₃, 300 MHz): δ 6.94–7.16 (m, 6H, H1-H4-H5), 6.57 (dt, 2H, H2), 3.33 (t, J=1.8 Hz, 4H, H3), 3.02 (s, 4H, H6), 2.46 (s, 6H, H7) ppm.

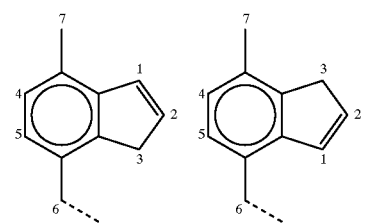

¹³C NMR (CDCl₃, 75 MHz): Isomer 1: 18.29 (CH₃), 33.82 (CH₂), 37.88 (CH₂), 124.70 (arom. CH), 128.00 (q-C), 127.78 (arom. CH), 130.49 (arom. CH), 133.07 (arom. CH), 134.45 (q-C), 141.7 (q-C), 143.51 (q-C); Isomer 2: 18.45 (CH₃), 33.72 (CH₂), 37.92 (CH₂), 38.22 (CH₂ ?), 125.95 (arom. CH), 126.65 (arom. CH), 130.12 (arom. CH), 130.60 (q-C), 132.15 (q-C), 133.53 (arom. CH), 142.40 (q-C), 142.72 (q-C).

EXAMPLE 15 rac- and meso-ethylenebis(7-methyl-4-indenyl) zirconium Dichloride

To a suspension of 18.0 g (62.8 mmol) of the product obtained in Example 14 in 200 ml anhydrous ether was added dropwise 82.5 ml 1.6 M BuLi (132.0 mmol) at −78° C. under an inert atmosphere. After cooling for 30 minutes the cooling bath was removed and the reaction mixture was allowed to warm to room temperature. After stirring for 2 hours at room temperature the solvent was removed in vacuo. The yellow solid was extracted with toluene until the toluene was colourless. The toluene was evaporated in vacuo and about 100 ml anhydrous toluene was added. After separating the insoluble solid the toluene solution was concentrated and crystallised at −30° C. yielding 3.15 g (7.05 mmol) product as yellow needles. The remaining solid was dissolved in anhydrous CH₂Cl₂, concentrated and crystallised at −30° C. yielding 0.82 g (1.84 mmol) product as orange prism shaped crystals. The yellow crystals were identified as the rac isomer and the orange crystals as the meso isomer.

rac isomer: ¹H NMR (CDCl₃, 300 MHz): δ 7.08–7.21 (dd, J=6.9 Hz, 4H, H), 6.72 (t, J=3.5 Hz, 2H, 5 ring), 6.67 (t, J=3.5 Hz, 2H, 5 ring), 4.48 (dd, 2H, 5 ring), 3.35 (m, 2H, bridge), 3.04 (m, 2H, bridge), 2.60 (s, 6H, CH₃) ppm. ¹³C NMR (CDCl₃, 75 MHz): δ 19.90 (CH₃), 36.58 (CH₂), 102.18 (CH, 5 ring), 108.48 (CH, 5 ring), 125.13 (CH, 6 ring), 126.48 (q-C), 126.55 (CH, 6 ring), 126.95 (q-C), 135.08 (q-C), 137.08 (q-C) ppm.

meso isomer: ¹H NMR (CDCl₃, 300 MHz): δ 7.14 (dd, J=3.45 Hz, 2H, 5 ring), 6.67 (m, 4H, 6 ring), 6.60 (t, J=3.45 Hz, 2H, 5 ring), 6.51 (dd, J=3.45 Hz, 2H, 5 ring), 3.39 (m, 4H, bridge), 2.33 (s, 6H, CH₃) ppm. ¹³C NMR (CDCl₃, 75 MHz): δ 19.62 (CH₃), 30.83 (CH₂), 99.30 (CH, 5 ring), 106.09 (CH, 5 ring), 121.52 (q-C), 122.76 (CH, 5 ring), 125.47 (CH, 6 ring), 125.75 (CH, 6 ring), 130.75 (q-C), 132.96 (q-C), 134.81 (q-C) ppm.

EXAMPLE 16

1,1'-dimethyl-4,4'-dimethyl-7,7'-diindenyl-1,2-ethane, 1,1'-dimethyl-7,7'-dimethyl-4,4'-diindenyl-1, 2-ethane, and 1,1'-dimethyl-4,7'-dimethyl-4',7-diindenyl-1,2-ethane To a solution of 50 ml 3.0 M CH₃MgBr (150 mmol) in anhydrous ether was added a solution of 8 g (25 mmol) of the product obtained in step (C) of Example 14 in 200 ml anhydrous THF over a period of 1 hour at 0° C. After addition of 30 ml the clear solution became cloudy. The reaction mixture was allowed to warm to room temperature and stirred for 2 hours, subsequently the solvent was evaporated in vacuo. After addition of 100 ml aqueous 10% HCl the white suspension was extracted with 100 ml $CH_2Cl_2$. After separation the combined suspensions of $CH_2Cl_2$ were filtered and after washing with pentane resulted in 4.2 g (13.4 mmol, 53%) white product.

$^1$H NMR ($CDCl_3$, 300 MHz): δ 6.94–7.10 (m, 4H, arom.), 6.23+6.16 (s, 2H, 5 ring), 3.21 (m, $CH_2$, 4H, 5 ring), 2.96 (s, $CH_2$, 4H, bridge), 2.59 (s, $CH_3$, 6H), 2.30–2.46 (m, 6H, $CH_3$) ppm.

EXAMPLE 17 rac- and meso-ethylenebis(1,7-dimethyl-4-indenyl) zirconium Dichloride

To a suspension of 1 g (3.18 mmol) of the product obtained in Example 16 in 40 ml anhydrous ether was added dropwise 4.2 ml 1.6 M BuLi (6.72 mmol) in hexane at −78° C. After addition the reaction mixture was allowed to warm to room temperature and subsequently stirred for 2 hours. The solvent was evaporated in vacuo and 50 ml anhydrous toluene was added. Subsequently 0.74 g (3.18 mmol) $ZrCl_4$ was added portionwise at room temperature upon the colour changed from red/pink to yellow/orange. The reaction mixture was stirred overnight and the suspension was centrifuged. The solvent of the clear solution was evaporated in vacuo, the yellow solid was dissolved in 20 ml toluene and concentrated. Crystallisation afforded 50 mg of the meso isomer as a beige powder. The supernatant was evaporated to dryness to afford the rac isomer.

rac isomer: $^1$H NMR ($CD_2Cl_2$, 300 MHz): δ 7.09 (d, J=6.9 Hz, aromatic, 2H), 6.93 (d, J=6.9 Hz, aromatic, 2H), 6.41 (d, J=3.30 Hz, 2H), 4.37 (d, J=3.30 Hz, 2H), 2.92–3.40 (m, 4H, bridge), 2.70 (S, 12H, $CH_3$) ppm. meso isomer: $^1$H NMR ($CD_2Cl_2$, 300 MHz): δ 6.88 (d, J=3.30 Hz, 2H), 6.57 (s, 4H, aromatic), 6.30 (d, J=3.30 Hz, 2H), 3.20–3.45 (m, 4H, bridge), 2.68 (s, 6H, $CH_3$), 2.52 (s, 6H, $CH_3$) ppm. $^{13}$C NMR ($CD_2Cl_2$, 75 MHz): δ 16.23 ($CH_3$), 21.20 ($CH_3$), 36.35 ($CH_2$, bridge), 100.64 (CH, 5 ring), 119.80 (q-C), 124.34 (CH, 6 ring), 125.28 (q-C), 127.23 (q-C), 127.34 (CH, 6 ring), 131.10 (CH, 5 ring), 135.88 (C), 138.09 (C) ppm.

EXAMPLE 18

1,2-bis(4-indenyl)ethane
(A) Synthesis of 2,2'-dibromo-1,2-diphenylethane 200 g (0.8 mol) of 2-bromobenzylbromide and 800 ml of dry THF were placed in a 2 L round bottom flask equipped with mechanical stirrer. Keeping this mixture at 20° C., 9.8 g of Mg (0.4 mol) was added in small portions. The reaction was started with a trace of iodine and stirred for 20 h. Workup was done by decanting the organic layer from the salts and washing the salts with 4 portions of 50 ml THF. The organic layers were combined and concentrated in vacuo. The resulting solid was dissolved in 400 ml dichloromethane and washed with 400 ml 5% HCl and twice with 200 ml water. The organic layer was separated from the aqueous layer, dried with $MgSO_4$, and concentrated in vacuo. Crystallization was done from ethanol. The product was isolated as white crystals (52 g). The remaining supernatant liquor was distilled to remove the starting material and by-products. The distilled product was crystallized from pentane and afforded an additional 12.6 g of product. Total product 64.6 g. Yield 48%.

$^1$H-NMR: 7.5 ppm (d,2H,aromatic), 7.2 ppm (m,4H, aromatic), 7.0 ppm (m,2H,aromatic), 3.0 ppm (s,4H,bridge); $^{13}$C-NM: 141.2 ppm (C4), 133.5 ppm (C2), 131.5 ppm (C5), 128,2 ppm (C1), 128,1 ppm (C6), 125.0 ppm (C3), 36.7 ppm (C7).

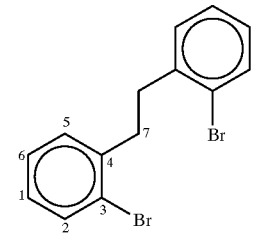

(B) Synthesis of 2,2'-diacrylicacid-1,2-diphenylethane

In a 2 L round bottom flask equipped with mechanical stirrer were placed 1 L of DMF, 0.39 g (1.74 mmol) of $Pd(OAc)_2$ and 2.14 g (10.5 mmol) of tri-o-tolylfosfine. This mixture was stirred for 10 min. at 50° C. Then 62 g (0.18 mol) of 2,2'-dibromo-1,2-diphenylethane, 22.8 ml water, 144.9 g $K_2CO_3$ and 36.3 ml (0.5 mol) of acrylic acid were added. This mixture was stirred for 4 h at 100° C. Workup was done by adding 1.5 L water with stirring to the solution. The Pd precipitate was removed by filtration and then the clear solution was carefully (in order to control gas evolution) acidified with concentrated HCl until pH 2. A white precipitate was formed which was isolated by filtration and dried in vacuo. Product 51 g. Yield 87%.

$^1$H-NMR: 7.25 ppm (d, 2H, double bond acid), 7.15 ppm (dd, 2H, aromatic), 6.82 ppm (dt, 2H, aromatic), 2.76 ppm (dt, 2H, aromatic), 5.85 ppm (d, 2H, double bond acid), 2.50 ppm (s, 4H, bridge).

(C) Synthesis of 2,2'-dipropionicacid-1,2-diphenylethane

In a 2 L three-necked round-bottom flask equipped with mechanical stirrer and reflux condenser were placed 52 g (0.16 mol) of 2,2'-diacrylicacid-1,2-diphenylethane, a solution of 13.2 g NaOH in 323 ml water and 0.8–1.0 g Raney-Ni (freshly made as a 50% solution in water). This mixture was heated to 90° C. and then 41 g of hydrazine monohydrate was added very slowly in order to control the gas formation. After addition, the mixture was stirred until gas formation stopped. Workup was performed by filtering the solution. The resulting clear solution was acidified to pH=2. A white solid was formed which was isolated by filtration. NMR showed that the reaction was not complete. The above procedure was repeated and afforded after workup 36.2 g of the product. Yield 70%.

$^1$H-NMR: 6.75 ppm (m, 8H, aromatic), 2.42 ppm (m, 8H, propionic acid), 2.05 ppm (m, 4H, bridge); $^{13}$C-NMR: 179.5 ppm (COOH), 145.0, 144.0 ppm (C4,C3), 135, 134 ppm (C2,C5), 131.7 ppm (C1,C6), 40.5, 39.5,32.5 ppm (C7,C8, C9).

(D) Synthesis of 4,4'-diindanoyl-1,2-ethane 800 g of polyphosphoric acid was placed in a 2 L roundbottom flask. This was heated to 100° C. and then 36 g of 2,2'-dipropionicacid-1,2-diphenylethane was added in one portion. The mixture was stirred for 4 h. Workup was done by pouring the reaction mixture into 500 ml ice water with vigorous stirring. The resulting mixture was saturated with $NH_4Cl$ and this mixture was extracted with three portions of 200 ml dichloromethane. The organic layers were combined and first washed with water, then with 10% $NaHCO_3$, and again with water. The organic layer was dried over $MgSO_4$ and concentrated in vacuo. The product was isolated as a brown solid. Product 25 g. Yield 78%.

¹H-NMR: 7.66 ppm (dd, 2H, aromatic), 7.35 ppm (m, 4H, aromatic), 3.00 ppm (m, 8H, 5-ring), 2.68 ppm (4H, bridge); ¹³C-NMR: 207.5 ppm (C1), 153.9 ppm (C4), 139.0 ppm (C9), 137.5 ppm (C8), 134.5 ppm (C5), 128.0 ppm (C6), 122.0 ppm (C7), 36.0 ppm (C2), 32.7 ppm (C10), 24.3 ppm (C3).

(E) Synthesis of 4,4'-diindenyl-1,2-ethane 5 g (17.2 mmol) of 4,4'-diindanoyl-1,2-ethane was suspended in 25 mLmethanol and 50 ml THF. 1.3 g (34.4 mmol) of NaBH$_4$ was added in portions keeping the mixture at room temperature. The reaction mixture was stirred for 24 h before another 4 equivalents of NaBH$_4$ was added. After 48 h the reaction was complete. Work up was done by pouring the mixture onto ice and adding dichloromethane to extract the water layer (three times). The organic layers were combined, dried on MgSO$_4$ and concentrated in vacuo. The product was isolated as a brown solid. This product was suspended in 100 ml toluene and 30 ml dichloromethane and warmed to 50° C. (reflux). Then 100 mg of p-toluenesulfonic acid was added and the reaction was stirred for 3 h. The organic layer was washed twice with 50 ml water and then the organic layer was dried over MgSO$_4$ and concentrated in vacuo. The isolated solid was extracted with pentane under reflux for 4 times. The bis(indene) product was isolated as a white solid (1.2 g). Yield 27%.

¹H-NMR: 7.23 ppm (m, 4H, aromatic), 7.06 ppm (dd, 2H, aromatic), 6.88 ppm (dt, 2H, 5-ring), 3.25 ppm (m, 4H, 5-ring), 3.05 ppm (s, 4H, bridge); ¹³C-NMR: 145.10 ppm (C4), 142.3 ppm (C9), 137.3 ppm (C8), 134.0 ppm (Cl), 132.7 ppm (C5), 127.1 ppm (C2), 125.0 ppm (C6), 119.3 ppm (C7), 37.9 ppm (C10), 34.3 ppm (C3).

EXAMPLE 19 rac- and meso-ethylenebis(4-indenyl)zirconium Dichloride 1.2 g (4.65 mmol) of 4,4'-diindenyl-1,2-ethane was dissolved in 50 ml of THF. This mixture was cooled to –60 ° C. and 6 ml of BuLi (9.6 mmol) was added slowly. After the addition the reaction temperature was raised to room temperature and the reaction mixture was stirred for 1 h. Then the THF was removed by evaporation. The remaining solid was suspended in 20 ml toluene. To this suspension, a suspension of 1 g (4.35 mmol) of ZrCl$_4$ in 5 ml of toluene was added dropwise at room temperature. This mixture was stirred for another 3 h. Workup was done by concentrating the mixture in vacuo. The remaining solid was extracted with CH$_2$Cl$_2$. The CH$_2$Cl$_2$ was evaporated and the remaining solid was extracted with ether. The ether layer was evaporated and the remaining solid was solved in toluene and placed cold. This afforded 130 mg of crystals of the rac-isomer. The last ether extraction was also cooled and this afforded 14 mg of meso-isomer.

rac-isomer: ¹H-NMR: 7.23 ppm (m, 4H, aromatic), 7.06 ppm (dd, 2H, aromatic), 6.88 ppm (dt, 2H, 5-ring), 3.25 ppm (m, 4H, 5-ring), 3.05 ppm (s, 4H, bridge). ¹³C-NMR: 140.0 ppm, 130.71 ppm, 126.93 ppm, 126.23 ppm, 125.19 ppm, 125.08 ppm, 124.9 ppm, 110.5 ppm, 102.0 ppm, 37.0 ppm. meso-isomer: ¹H-NMR: 7.26 ppm (d, 2H, aromatic), 7.08 ppm (m, 2H, 5-ring), 6.88 ppm (dd, 2H, aromatic), 7.72 ppm (d, 2H, aromatic), 6.64 ppm (t, 2H, 5-ring), 6.48 ppm (dd, 2H, 5-ring), 3.40 ppm (m, 4H, bridge).

EXAMPLE 20

1,1'-dimethyl-4,4'-diindenyl-1,2-ethane 5 g (17.2 mmol) of 4,4'-diindanoyl-1,2-ethane was suspended in 50 ml of THF and slowly added to a solution of 12.6 ml (37.8 mmol) MeMgBr in ether at 0° C. After the addition, the reaction mixture was stirred for 1 h at 0° C. and 5 h at 30° C. Workup was done by pouring the reaction mixture into ice-water. The organic layer was diluted with ether and separated from the water layer. The water layer was extracted twice with ether. The organic layers were combined, dried on MgSO$_4$ and concentrated in vacuo. The isolated product was dissolved in 100 ml toluene. To this solution, 100 mg of p-toluenesulfonic acid was added and the mixture was stirred for 2 h at room temperature. Then the toluene layer was washed twice with 50 ml of water, dried over MgSO$_4$, and concentrated in vacuo. This afforded 2 g of crude product which was extracted with pentane. The pentane layers were combined and concentrated in vacuo. The isolated yellow oil was chromatographed over silica with 9:1 hexane: ethylacetate. 1.2 g of pure product was isolated as a white solid. Yield 24%.

¹H-NMR: 7.29 ppm (t, 2H, aromatic), 7.21 ppm (dd, 2H, aromatic), 7.08 ppm (dd, aromatic), 6.18 ppm (m, 2H, 5-ring), 3.22 ppm (m, 4H, 5-ring), 3.03 ppm (s, 4H, bridge), 2.16 ppm (s, 6H, CH$_3$). ¹³C-NMR: 146.28 ppm (C4), 142.72 ppm (C9), 140.40 ppm (C1), 137.07 ppm (C8), 128.38 ppm (C5), 126.81 ppm (C6), 124.80 ppm (C7), 117.03 ppm (C2), 36.16 ppm (C10), 33.92 ppm (C3), 13.09 ppm(C11).

EXAMPLE 21 rac- and meso-ethylenebis(1-methyl-4-indenyl) zirconium Dichloride 1.2 g (4.2 mmol) of 1,1'-dimethyl-4,4'-diindenyl-1,2-ethane was dissolved in 30 ml of THF and cooled to –60° C. Then 5.8 ml (9 mmol) of BuLi was added slowly. After addition of the BuLi, the temperature was raised to room temperature and the mixture was stirred for 2 h. Then the THF was evaporated in vacuo and the remaining solid was suspended in 20 ml of toluene. A suspension of 1 g (4.3 mmol) of ZrCl$_4$ in 5 ml of toluene was added in portions at room temperature. After 72 h stirring the LiCl was removed by centrifugation and the clear toluene layer was concentrated in vacuo. The remaining solid was extracted 4 times with 40 ml diethylether and the ether layers were combined and concentrated in vacuo. The remaining solid was dissolved in toluene and crystallized. This gave the meso-isomer (35 mg, purity 87% contaminated by some rac-isomer). The remaining solvent was evaporated in vacuo and the solid suspended in ether. The clear ether layer was separated from the solid by centrifugation. The solid was the rac-isomer (125 mg, purity 93% contaminated with 7% meso-isomer).

rac-isomer: 1H-NMR: 7.36 ppm (d, 2H, aromatic), 6.86 ppm (dd, 2H, aromatic), 6.67 ppm (d, 2H, aromatic), 6.36 ppm (d, 2H, 5-ring), 4.00 ppm (m, 2H, 5-ring), 2.65 ppm (m, 4H, bridge), 2.40 ppm (s, 6H, CH$_3$). ¹³C-NMR: 140.05 ppm, 129.80 ppm, 126.46 ppm, 125.82 ppm, 125.09 ppm, 124.38 ppm, 122.78 ppm, 118.91 ppm, 100.02 ppm, 36.54 ppm, 13.00 ppm. meso-isomer: ¹H-NMR: 7.20 ppm (d, 2H, aromatic), 6.70 ppm (dd, 2H, aromatic), 6.38 ppm (d, 2H, aromatic), 6.25 ppm (d, 2H, 5-ring), 6.19 ppm (d, 2H, 5-ring), 2.85 ppm (m, 4H, bridge), 2.55 ppm (s, 6H, CH$_3$). ¹³C-NMR: 133.93 ppm, 131.41 ppm, 126.00 ppm, 125.74 ppm, 125.28 ppm, 122.36 ppm, 121.38 ppm, 117.46 ppm, 95.80 ppm, 30.63 ppm, 12.74 ppm.

EXAMPLE 22

1,2-bis(7-tert-butyl-4-indenyl)ethane (A) Synthesis of 1,2-bis(p-tert-butyl-benzene)ethane 200 ml of anhydrous THF, 3.35 g (138 mmol) of Mg turnings and a crystal of iodine were added to a 3-neck 500 ml round-bottom flask equipped with a reflux condenser. A solution of 56.6 g (250 mmol) of 4-tert-butyl-benzylbromide in 50 ml THF was added dropwise in about one hour to this. The reaction-mixture was refluxed for 5 hours, then allowed to cool to room temperature. The solvent was evaporated in vacuo and the remaining white solid was treated with 300 ml hexane and 300 ml aqueous HCl (10%). A large amount of white solid remained undissolved. By extraction with hexane and crystallisation, 4.95 g pure product could be isolated. The in hexane "undissolved" white solid yielded another 25.6 g of pure product. Total yield 30.55 g (104 mmol)=83%.

$^1$H-NMR (CDCl$_3$): 7.40 ppm (d, 2H, aromatic), 7.25 ppm (d, 2H, aromatic), 2.98 ppm (s, 4H, bridge), 1.41 ppm (s, 18H, CH$_3$). $^{13}$C-NMR (CDCl$_3$): 148.8 ppm (C), 139.0 ppm (C), 128.0 ppm (CH), 125.0 ppm (CH), 37.2 (CH$_2$, bridge), 34.37 ppm (CMe$_3$), 31.42 (CMe$_3$).

(B) Reaction with 3-chloropropionylchloride 33.2 g of AlCl$_3$ (109 mmol) and 90 ml of CH$_2$Cl$_2$ were charged in a 500 ml flask supplied with a 250 ml dropping funnel. The slurry was cooled to 0° C. and 30.6 g of 3-chloropropionylchloride was added dropwise in about 10 min. The reaction mixture was stirred for 30 minutes at 0° C. and then a solution of 1,2-bis(para-tert-butylbenzene)ethane 30.55 g, 104 mmol in 400 ml CH$_2$Cl$_2$ was added dropwise in 2.5 hr. After addition, stirring was continued an extra 1.5 hr at 0° C. NMR analysis showed a complete conversion. The reaction mixture was quenched with ice and 37% HCl; the aqueous layer was extracted with CH$_2$Cl$_2$. After drying over MgSO$_4$ and evaporation of solvent, 38.9 g product could be isolated. Yield 95%.

$^1$H-NMR (CDCl$_3$): δ 7.7–7.1 m, 6H aromatic), 3.88(t, 4H), 3.30(t, 4H), 3.17(s, 4H bridge), 1.26(s, 18H, CH$_3$). $^{13}$C-NMR δ 199.5(CO), 155.1(C), 14.9(C), 134.5(C), 129.1 (CH), 128.6(CH), 122.8(CH), 43.8(COCH$_2$CH$_2$CL), 39.1 (COCH$_2$CH$_2$CL), 35.9(CMe$_3$), 34.8(CH$_2$, bridge), 31.0(CME$_3$).

(C) Ring closure with H$_2$SO$_4$

The product of step 2 above was dissolved in 210 ml CH$_2$Cl$_2$ together with 10 mg Bu$_4$NHSO$_4$ in a 500 ml flask. 106 ml of 96% H$_2$SO$_4$ was added in 10 minutes. The reaction mixture was refluxed for 4.5 hrs. The mixture was poured onto ice and NaOH pellets were added until pH 7 was obtained. This was extracted with 300 ml ether. However, the product was only partially soluble. By partial evaporation of solvent and cooling to −25° ° C., 2.7 g of pure product could be isolated. The yellow solid which had not dissolved during the ether extraction was also a rather pure product; 11.9 g. Total yield 14.6 g indanone (36.3 mmol) =73%.

$^1$H-NMR (CDCl$_3$): δ 7.26(s,2H), 7.16(s,2H), 3.31 (s, 4H, bridge), 3.06(m, 4H, CH$_2$), 2.65(s, 4H, CH$_2$), 1.30(s, 18H, CH$_3$). $^{13}$C-NMR δ 207.5 (CO), 158.5(C), 156.5(C), 142.5 (C), 132.0(C), 126.7(CH), 121.0(CH), 37.5(CH$_2$, ring), 35.5(CMe$_3$), 33.2(CH$_2$, bridge), 31.5(CMe$_3$), 25.8(CH$_2$, ring).

(D) Reduction with NaBH$_4$ and successive dehydration

The product from above was suspended in 200 ml THF and 100 ml methanol. At 0° C. small portions of solid NaBH$_4$ were added. In total 6.7 g (177 mmol) NaBH$_4$ were added in 3.5 hrs at 0° C. and subsequently stirred over-night at 20° C. Work-up was performed by careful addition of ice and aqueous HCl until pH 1 was reached. The organic solvents were distilled off in vacuo and the residue extracted with ether. The product (13.0 g) was a mixture of the indanol and the indene (caused by acidic dehydration with aqueous HCl). The dehydration was completed by addition of 400 ml benzene and 180 mg p-toluenesulphoic acid and refluxing for 4 hrs in a Dean-Stark apparatus. Workup was carried out by washing with aqueous NaHCO$_3$, drying and evaporation of the solvent. This afforded 11.2 g (30.3 mmol) of pure product.

$^1$H NMR (CDCl$_3$): δ 7.44(d, 2H), 7.16(d, 2H), 6.98 (dt, 2H), 6.53 (dt, 2H), 3.43(bs, 4H, CH$_2$, ring), 3.13(s, 4H, bridge), 1.38(s, 18H, CH$_3$). $^{13}$C-NMR δ 148.5(C), 144.1(C), 141.2(C), 134.1(C), 133.7(CH), 130.3(CH), 123.8(CH), 119.5(CH), 39.7(CH$_2$, ring), 36.0(CH$_2$, bridge), 35.0(CMe$_3$), 32.0(CMe$_3$).

EXAMPLE 23 ethylenebis(7-tert-butyl-4-indenyl)zirconium Dichloride

To a solution of 6.0 g (16.2 mmol) of bis(indene) above in 200 ml ether was added at −80° C. 21.3 ml of a hexane solution of 1.6 M n-BuLi (34.1 mmol) during 15 minutes. The temperature was gradually raised to 20° C. and the reaction stirred for another 2 hrs. This dianion solution was cooled to −40° C. and a slurry of 3.82 g (16.4 mmol) ZrCl$_4$ in 50 ml ether was added. The reaction mixture was allowed to warm up to room temperature and stirred overnight. Isolation and purification of the zirconocene proved to be tedious. The reaction-mixture was evacuated to dryness. This was extracted twice with toluene and the toluene reduced in volume until crystallization was induced. Attempts to completely separate the rac- and meso-isomers were unsuccessful. By this labourious purification method only ca. 250 mg pure zirconocene (mixture of rac/meso isomers in about 15/85 ratio) could be obtained.

$^1$H-NMR (CD$_2$Cl$_2$): δ 7.18(d, 2H), 7.12(d, 2H), 6.77(d, 2H), 6.45(m, 2H), 6.40(m, 2H), 3.55–3.20(m, 4H, bridge), 1.15(s, 18H, CH$_3$).

EXAMPLE 24

1,2-bis(1-fluorenyl)ethane (A) Synthesis of 1-bromomethylfluorene

Fluorene-1-carboxylic acid was purchased from Aldrich. It was reduced as described in J. Am. Chem. Soc. 1961, 83, 417 via the methyl ester to 1-hydroxymethylfluorene $^1$H NMR (CDCl$_3$): δ 4.84 ppm (CH$_2$), 3.89 ppm (CH$_2$). 4.1 g (21 mmol) 1-hydroxymethylfluorene dissolved in 60 ml THF was slowly added to 2.54 g PBr$_3$ in 10 ml THF at −5° C. The orange solution was stirred for 1.5 hrs at −5° C. then stirred for 16 hrs at room temperature. This was then poured into iced water, allowed to settle and 5.1 g of 1-bromomethylfluorene was isolated on a frit as an off-white powder. $^1$H NMR (CDCl$_3$): δ 4.65 ppm (CH$_2$), 3.97 ppm (CH$_2$).

(B) Synthesis of 1,2-bis(1-fluorenyl)ethane 5.1 g, 19.6 mmol 1-bromomethylfluorene dissolved in 50 ml THF was added dropwise to 0.24 g, 9.9 mmol Mg in 10 ml THF. After addition the Grignard was refluxed for 2 hrs, cooled and water/aqueaous HCl added. After work-up this afforded 1.5 g of CH$_2$CH$_2$(1-fluorenyl)$_2$ as a beige powder. 1H NMR (CDCl$_3$): δ 3.81 ppm (CH$_2$), 3.14 ppm (CH$_2$).

EXAMPLE 25 ethylenebis(1-fluorenyl)zirconium Dichloride 1.5 g, 4.2 mmol of 1,2-bis(1-fluorenyl)ethane was suspended in 50 ml ether and 2 equiv n-BuLi (5.2 ml of a 1.6

M solution) was added at 0° C. via syringe. This was stirred for 40 minutes at room temperature during which the solution became dark red. The ether was removed under vacuum to give the dianion as a dark oily solid. This was washed with 2×20 ml hexane. To a suspension of the dianion in 50 ml toluene was added 0.98 g $ZrCl_4$ as a suspension in toluene at room temperature. The dark solution rapidly became a lighter red-brown. This was stirred for 16 hrs at room temperature. The orange-red toluene solution was separated from the light-red toluene-insoluble powder by centrifugation.

EXAMPLES 26–34

Polymerization of Propylene

A 5 L reactor was loaded with 1.6 Kg propene. In the premix (in toluene), 500 molar equivalents of MAO and 4 $\mu$moles of the metallocene were stirred in a drybox at 20° C. for a time comprised between 1.5 hours and over-night. A further amount of MAO was injected into the autoclave containing the liquid propene, and subsequently (5 minutes later) the premix added. The total Zr:MAO ratio was 1:5000. The reactor was held at 30° C. for 1 minute and then the temperature raised with a temperature gradient of 4° C./minute to 50° C. Polymerization was continued for a further 60 minutes at 50° C. The polymerization activities and the data relating to characterization of the polymers obtained are reported in Table 2. The NMR characterization of some of the obtained polymers is reported in Table 3.

EXAMPLES 35–43

Copolymerization of Propylene with Ethylene

A 25 L reactor was loaded with 7. 5 Kg propene and with a ethylene/propylene feed ratio ca. 6 mol % (liquid phase). This is equivalent to a 3.3 bar ethylene overpressure. The feed ratio was kept constant throughout the polymerization by adding ethylene on demand. The total amount of MAO added was kept constant at 11.0 g. This led to variable Zr:MAO ratios. The premix was with a Zr:MAO ratio of 1:500. The further MAO was injected into the autoclave and subsequently (5 minutes later) the premix added at 50° C. The copolymerizations were essentially isothermal with typical initial exotherms of 1–5° C. being observed. The copolymerization reactions were continued at 50° C. The polymerization data and the data relating to characterization of the polymers obtained are reported in Table 2.

EXAMPLE 44

1,2-bis(4-indenyl)ethane (A) Synthesis of 2,2'-diiodo-1,2-diphenylethane

In a 1 L beaker 460 ml of water, 56.8 ml of 37% HCl and 21.2 g (0.1 mol) of 2,2'-diamino-1,2-diphenylethane were mixed. The mixture was heated until full dissolving of diamine and then rapidly cooled with intensive stirring down to 2–3° C. with the use of ice/NaCl bath and adding of small pieces of ice. A suspension of diamine hydrochloride was formed. The solution of 14.5 g of NaNO2 in 90 ml of H2O was added slowly with stirring to the suspension. The temperature was always kept at 2–3° C. After full addition of NaNO2 the solution became yellow and transparent. After 15 min. it was treated with solid urea until full evacuation of N2 (destruction of NaNO2 excess). To the resulting solution was added a cold solution of 15.5 g of KI in 143 ml of H2O. The formation of dark solid and evacuation of N2 took place. Then the reaction mixture was boiled during 30 min., cooled and the aqueous solution was decanted from the black solid. This solid was heated 30 min. with 10% aqueous NaOH (to remove phenols) and then washed twice with H2O. The resulting dark solid was recrystallized twice from ethanol giving slightly-yellow needle crystals of the product. The yield was about 40%.

(B) Synthesis of 2,2'-diacrylicacid-1,2-diphenylethane

In a 500 ml round-bottomed flask equipped with magnetic stirrer were placed under Ar atmosphere, 180 ml of DMF, 43.4 g (0.1 mol) of 2,2'-diiodo-1,2-diphenylethane, 20 ml of H2O, 41.1 g (0.3 mol) of K2CO3, 33 g (0.3 mol) of potassium acrylate and 0.11 g (5 mmol) of Pd(OAc)2. The reaction mixture was stirred at 100° C. during 7 h, then filtered from black Pd precipitate and diluted with 1.5 L of H2O. This solution was extracted with ether, the water layer was separated, heated on the water bath to remove traces of ether, cooled and acidified with 37% HCl until pH of about 2. The precipitated product was filtered, cleaned with small portions of water and dried in vacuum. Yield: 98%.

(C) Synthesis of 2.2'-dipropionicacid-1,2-diphenylethane

In a 500 ml round-bottomed flask, equipped with condenser, magnetic stirrer and dropping funnel were placed 16.1 g (0.05 mol) of 2,2'-diacrylicacid-1,2-diphenylethane, a solution of 4.1 g of NaOH in 100 ml of H2O and 0.2–0.3 g of freshly prepared Raney-Ni. The reaction mixture was heated up to 90° C. under stirring and 12 g of 85% hydrazine hydrate was added drop wisely during 15 min. Heating and stirring were continued until full evacuation of N2. Then the reaction mixture was cooled, filtered from Ni precipitate and acidified by 37% HCl (pH ~2). The product was precipitated as white powder, filtered, cleaned several times with small portions of H2O and dried in vacuum. Yield: 90%.

(D) Synthesis of 4,4'-diindanonyl-1,2-ethane

To the polyphosphoric acid, prepared by the partial addition of 270 g of P2O5 into 98 ml of 85% phosphoric acid at 130–150° C. until full homogenization and cooled down to 100° C. was added as one portion under vigorous stirring a thin powder of 16.3 g (0.05 mol) of 2,2'-dipropionicacid-1, 2-diphenylethane. The reaction mixture was stirred under this temperature during 3 h. It became homogenious and changed colour from black to brown. Then it was poured into 1 L of water—ice mixture under vigorous stirring. Resulting mixture was saturated with NH4Cl and extracted with 5×200 ml CH2Cl2. Organic parts were combined, cleaned twice with small portions of water, 10% aqueous NaHCO3 and again water untill neutral reaction. Dried with Na2SO4. Solvent was removed and the product was obtained as a red crystalline solid. Yield: 95%.

(E) Synthesis of 4,4'-diindenyl-1,2-ethane

It was worked according to the procedure described in steps (d) and (e) of Example 1. The yield was about 70%.

EXAMPLE 45

1,2-bis(2-methyl-4-indenyl)ethane (A) Synthesis of 2,2'-dimethyl-4,4'-diindanonyl-1,2-ethane It was worked according to the procedure described in steps (A) to (D) of Example 44, except that methacrylic acid or potassium methacrylate were used instead of acrylic compounds. However, the resulting mixture of diacids contained about 25% of "wrong" acrylic type acidic groups which are stable for hydrogenization either on Raney Ni and Adams PtO2. In order to prevent undesiderable Friedel-Krafts reaction with the participation of these double bonds during cyclization, partially hydrogenated product was boiled in benzene fo 3 h in the presence of 1 g of benzoyl peroxide. Benzene was removed under reduced pressure, the residue dissolved in diethyl ether and filtered from unsoluble polymeric product. After removing of ether and drying in vacuum it was cyclized in polyphosphoric acid under conditions described in the step (D) of Example 44. The product was obtained as a yellow oil. The yield of not pure target compound is about 35%. This was used without further purification.

(B) Synthesis of 2,2'-dimethyl-4,4'-diindenyl-1,2-ethane

It was worked according to the procedure described in steps (d) and (e) of Example 1. The resulting oil contained 14% of the target product as determined by GC-mass.

TABLE 1

| EXAMPLE | Zr ($\mu$mol) | Al/Zr (mol) | ethylene (g) | propylene (g) | hexane (g) | toluene (g) | T (° C.) | time (min) | P (bar) | yield (g) | activity (Kg$_{pol}$/g$_{cat}$) | I.V. (dL/g) | $C_2$ (% w) | ENB (% w) |
|---|---|---|---|---|---|---|---|---|---|---|---|---|---|---|
| 7 | 9 | 500 | — | — | 0 | 39 | 40 | 30 | 2.0 | 1.15 | 0.29 | 0.82 | 61 | 0 |
| 8 | 9 | 500 | — | — | 0 | 39 | 40 | 30 | 2.0 | 1.05 | 0.26 | 0.18 | 61 | 21.3 |
| 9 | 3.75 | 1000 | 36.0 | 24.0 | 1326 | 0 | 50 | 26 | 8.9 | 77 | 225 | 2.01 | 61.9 | 0 |
| 10 | 3.75 | 1000 | 24.8 | 16.6 | 1326 | 0 | 50 | 60 | 8.9 | 50 | 146 | 1.80 | 63 | 2.4 |
| 11 | 1.88 | 1000 | 117.6 | 849.6 | 386.6 | 0 | 30 | 120 | 15.2 | 129 | 115.0 | 9.72 | 73.0 | 0 |
| 12 | 1.88 | 1000 | 95.4 | 851.4 | 379.0 | 0 | 30 | 90 | 14.2 | 71 | 84.5 | 9.16 | 71.7 | 0 |
| 13 | 1.88 | 1000 | 70.8 | 853.5 | 369.3 | 0 | 30 | 90 | 13.1 | 85 | 101.0 | 7.42 | 67.0 | 0 |

TABLE 2

| EXAMPLE | metallocene type | ($\mu$mol) | Al/Zr (mol) | activity (Kg$_{pol}$/g$_{Zr}$h) | $C_2$ units (mol %) | LVN (dl/g) |
|---|---|---|---|---|---|---|
| 26 | Ex. 15 rac-isomer | 4 | 5000 | 10 | 0 | 1.12 |
| 27 | Ex. 15 meso-isomer | 4 | 5000 | 204 | 0 | 0.39 |
| 28 | Ex. 19 rac-isomer | 4 | 5000 | 27 | 0 | 0.60 |
| 29 | Ex. 19 meso-isomer | 4 | 5000 | 25 | 0 | — |
| 30 | Ex. 21 rac-isomer | 4 | 5000 | 12 | 0 | — |
| 31 | Ex. 21 meso-isomer | 4 | 5000 | 3 | 0 | — |
| 32 | Ex. 17 rac-isomer | 4 | 5000 | 1 | 0 | 1 |
| 33 | Ex. 17 meso-isomer | 4 | 5000 | 1 | 0 | 1 |
| 34 | Ex. 21 15/85 rac/meso | 4 | 5000 | 123 | 0 | 0.42 |
| 35 | Ex. 15 rac-isomer | 4 | 5000 | 230 | 59.6 | 3.85 |
| 36 | Ex. 15 meso-isomer | 0.5 | 40000 | 5347 | 74.5 | 2.88 |
| 37 | Ex. 19 rac-isomer | 0.5 | 40000 | 2014 | 66.7 | 8.71 |
| 38 | Ex. 19 meso-isomer | 1 | 20000 | 781 | — | 2.32 |
| 39 | Ex. 21 rac-isomer | 0.5 | 40000 | 1440 | — | 6.62 |
| 40 | Ex. 21 meso-isomer | 1 | 20000 | 720 | — | 4.36 |
| 41 | Ex. 17 rac-isomer | 1 | 20000 | 380 | — | — |
| 42 | Ex. 17 meso-isomer | 0.5 | 40000 | 55 | — | — |
| 43 | Ex. 21 rac/meso 15/85 | 0.5 | 40000 | 2188 | 61.6 | 1.41 |

TABLE 3

| EXAMPLE | 1,2 insertion (%) | 2,1 insertions (%) | 1,2 insertions (%) | mmmm (mol %) | mm (mol %) | mr (mol %) | rr (mol %) |
|---|---|---|---|---|---|---|---|
| 26 | 99.7 | 0.0 | 0.3 | 64.9 | 76.8 | 15.8 | 7.4 |
| 27 | 100 | 0.0 | 0.0 | 8.2 | 28.3 | 48.8 | 22.9 |
| 28 | 99.4 | 0.6 | 0.0 | 36.6 | 55.7 | 29.9 | 14.3 |

What is claimed is:

1. A metallocene compound of formula (I):

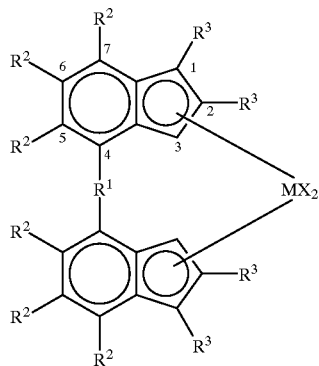

(I)

wherein $R^1$ is a $(CH_2)_2$ group;

$R^2$ and $R^3$, which may be identical or different, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals, or $C_7$–$C_{20}$ aralkyl radicals and can contain atoms of Si or Ge, and in addition two substituents $R^2$ and $R^3$ adjacent on the same indenyl can form a ring containing from 4 to 8 carbon atoms;

M is an atom of a transition metal selected from the group consisting of groups 3, 4, 5 or 6 or the lanthanides or the actinides in the Periodic able of the Elements (new IUPAC version); and the substituents X which may be identical or different, are hydrogen atoms, halogen atoms, R OR, $SR_1$, $NR_2$, or $PR_2$ groups, wherein the substituents R are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals, or $C_7$–$C_{20}$ aralkyl radicals and can contain atoms of Si or Ge, wherein the substituents $R^2$ in the 5 and 6 positions and the substituents $R^3$ in the 1 positions are hydrogen atoms, and the substituents $R^2$ in the 7 positions are different from hydrogen.

2. A metallocene compound of formula (I):

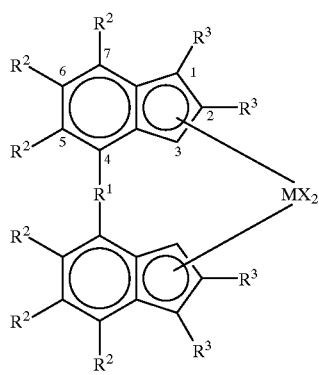

(I)

wherein $R^1$ is a $(CH_2)_2$ group;
the $R^2$ substituents are hydrogen;

the $R^3$ substituents, which may be identical or different, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ radicals, or $C_7$–$C_{20}$ aralkyl radicals and can contain atoms of Si or Ge;

M is an atom of a transition metal selected from the group consisting of groups 3, 4, 5 or 6 or the lanthanides or the actinides in the Periodic able of the Elements (new IUPAC version); and the substituents X which may be identical or different, are hydrogen atoms, halogen atoms, R OR, $SR_1$, $NR^2$, or $PR_2$ groups, wherein the substituents R are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals, or $C_7$–$C_{20}$ aralkyl radicals and can contain atoms of Si or Ge, wherein the substituents $R^3$ in the 1 positions are hydrogen atoms, and the substituents $R^3$ in the 2 positions are different from hydrogen.

3. A metallocene compound of formula (I):

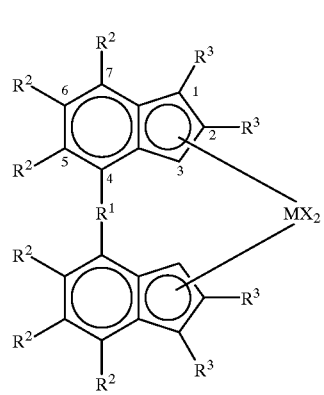

(I)

wherein $R^1$ is a $(CH_2)_2$ group;

$R^2$ and $R^3$, which may be identical or different, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals, or $C_7$–$C_{20}$ aralkyl radicals and can contain atoms of Si or Ge, and in addition two substituents $R^2$ and $R^3$ adjacent on the same indenyl can form a ring containing from 4 to 8 carbon atoms;

M is an atom of a transition metal selected from the group consisting of groups 3, 4, 5 or 6 or the lanthanides or the actinides in the Periodic able of the Elements (new IUPAC version); and the substituents X which may be identical or different, are hydrogen atoms, halogen atoms, R OR, $SR_1$, $NR^2$, or $PR_2$ groups, wherein the substituents R are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals, or $C_7$–$C_{20}$ aralkyl radicals and can contain atoms of Si or Ge, wherein the substituents $R^2$ in the 5 and 7 positions and the substituents $R^3$ in the 1 positions are hydrogen atoms, and the substituents $R^2$ in the 6 positions are different from hydrogen.

4. A metallocene compound of formula (I):

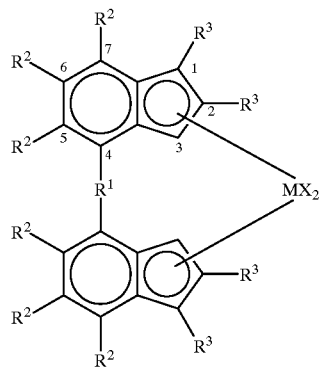
(I)

wherein $R^1$ is a $(CH_2)_2$ group;

$R^2$ and $R^3$, which may be identical or different, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals, or $C_7$–$C_{20}$ aralkyl radicals and can contain atoms of Si or Ge, and in addition two substituents $R^2$ and $R^3$ adjacent on the same indenyl can form a ring containing from 4 to 8 carbon atoms;

M is an atom of a transition metal selected from the group consisting of groups 3, 4, 5 or 6 or the lanthanides or the actinides in the Periodic able of the Elements (new IUPAC version); and the substituents X which may be identical or different, are hydrogen atoms, halogen atoms, R OR, $SR_1$, $NR_2$, or $PR_2$ groups, wherein the substituents R are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals, or $C_7$–$C_{20}$ aralkyl radicals and can contain atoms of Si or Ge, wherein the substituents $R^2$ in the 7 positions and the substituents $R^3$ in the 1 positions are hydrogen atoms, the substituents $R^2$ in the 5 and 6 positions form an alkylene ring, and the substituents $R^3$ in the 2 positions are different from hydrogen.

5. A metallocene compound of formula (I):

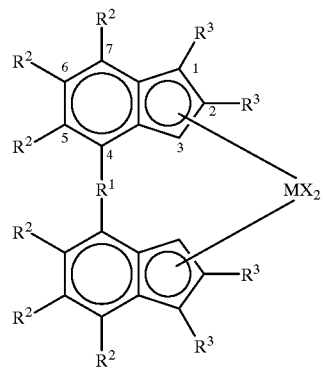
(I)

wherein $R^1$ is a $(CH_2)_2$ group;

$R^2$ and $R^3$, which may be identical or different, are hydrogen atoms, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals, or $C_7$–$C_{20}$ aralkyl radicals and can contain atoms of Si or Ge, and in addition two substituents $R^2$ and $R^3$ adjacent on the same indenyl can form a ring containing from 4 to 8 carbon atoms;

M is an atom of a transition metal selected from the group consisting of groups 3, 4, 5 or 6 or the lanthanides or the actinides in the Periodic able of the Elements (new IUPAC version); and the substituents X which may be identical or different, are hydrogen atoms, halogen atoms, R OR, $SR_1$, $NR_2$, or $PR_2$ groups, wherein the substituents R are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkaryl radicals, or $C_7$–$C_{20}$ aralkyl radicals and can contain atoms of Si or Ge, wherein the substituents $R^3$ in the 1 positions are hydrogen atoms, and the substituents $R^2$ in the 6 and 7 positions form an alkylene ring.

6. The metallocence compound according to claim 1, wherein the substituents $R^3$ at the 2 positions are hydrogen atoms.

* * * * *

UNITED STATES PATENT AND TRADEMARK OFFICE
CERTIFICATE OF CORRECTION

PATENT NO. : 6,369,254 B1
DATED : April 9, 2002
INVENTOR(S) : Luigi Resconi et al.

It is certified that error appears in the above-identified patent and that said Letters Patent is hereby corrected as shown below:

<u>Title page,</u>
Item [73], entitled "Inventors", please change "Ren' Ernst" to -- Rene Ernst --.

<u>Column 31,</u>
Line 33, please change "able" to -- Table --.
Line 36, please insert a comma after "R".
Line 36, please delete the subscript "$_1$" from "$SR_1$".

<u>Column 32,</u>
Line 4, please change "$C_7$-$C_{20}$ radicals" to -- $C_7$-$C_{20}$ alkaryl radicals --.
Line 8, please change "able" to -- Table --.
Line 11, please insert a comma after "R".
Line 11, please delete the subscript "$_1$" from "$SR_1$".
Line 11, please change "$NR^2$" to -- $NR_2$ --.
Line 54, please change "able" to -- Table --.
Line 57, please insert a comma after "R".
Line 57, please delete the subscript "$_1$" from "$SR_1$".
Line 57, please change "$NR^2$" to -- $NR_2$ --.

<u>Column 33,</u>
Line 34, please change "able" to -- Table --.
Line 37, please insert a comma after "R".
Line 37, please delete the subscript "$_1$" from "$SR_1$".
Line 46, please change "$R^3$" to -- $R^2$ --.

<u>Column 34,</u>
Line 24, please change "$C_6$-$C20$" to -- $C_6$-$C_{20}$ --.
Line 32, please change "able" to -- Table --.

UNITED STATES PATENT AND TRADEMARK OFFICE
CERTIFICATE OF CORRECTION

PATENT NO. : 6,369,254 B1
DATED : April 9, 2002
INVENTOR(S) : Luigi Resconi et al.

It is certified that error appears in the above-identified patent and that said Letters Patent is hereby corrected as shown below:

<u>Column 34 cont'd,</u>
Line 35, please insert a comma after "R".
Line 35, please delete the subscript "$_1$" from "$SR_1$".
Line 35, please change "$NR^2$" to -- $NR_2$ --.
Line 35, please change "$PR^2$ to -- $PR_2$ --.

Signed and Sealed this

First Day of October, 2002

Attest:

JAMES E. ROGAN
Attesting Officer     *Director of the United States Patent and Trademark Office*